US008729296B2

(12) United States Patent
Fast et al.

(10) Patent No.: US 8,729,296 B2
(45) Date of Patent: *May 20, 2014

(54) GENERATION OF PEROXYCARBOXYLIC ACIDS AT ALKALINE PH, AND THEIR USE AS TEXTILE BLEACHING AND ANTIMICROBIAL AGENTS

(75) Inventors: Jonathan P. Fast, St. Paul, MN (US); Robert D. P. Hei, Baldwin, WI (US); Richard Staub, Lakeville, MN (US); Thomas J. Dürrschmidt, Hilden (DE); Peter J. Forth, Dusseldorf (DE); Junzhong Li, Apple Valley, MN (US); David D. McSherry, St. Paul, MN (US); Thomas Merz, Hilden (DE); Johannes G. Winter, Unterhaching (DE)

(73) Assignee: Ecolab USA Inc., Saint Paul, MN (US)

( * ) Notice: Subject to any disclaimer, the term of this patent is extended or adjusted under 35 U.S.C. 154(b) by 106 days.

This patent is subject to a terminal disclaimer.

(21) Appl. No.: 13/331,104

(22) Filed: Dec. 20, 2011

(65) Prior Publication Data
US 2012/0172439 A1 Jul. 5, 2012

Related U.S. Application Data

(60) Provisional application No. 61/427,965, filed on Dec. 29, 2010, provisional application No. 61/427,951, filed on Dec. 29, 2010.

(51) Int. Cl.
*C07C 409/24* (2006.01)

(52) U.S. Cl.
USPC .............. 562/6; 562/2; 562/3; 562/4; 422/28; 424/616; 568/568

(58) Field of Classification Search
None
See application file for complete search history.

(56) References Cited

U.S. PATENT DOCUMENTS

| | | |
|---|---|---|
| 2,955,905 A | 10/1960 | Davies et al. |
| 2,995,524 A | 8/1961 | Wylie |
| 3,256,198 A | 6/1966 | Matzner |
| 3,272,750 A | 9/1966 | Chase |
| 3,432,546 A | 3/1969 | Oringer et al. |
| 3,847,830 A | 11/1974 | Williams et al. |
| 3,925,234 A | 12/1975 | Hachmann et al. |
| 4,003,841 A | 1/1977 | Hachmann et al. |
| 4,013,575 A | 3/1977 | Castrantas et al. |
| 4,051,058 A | 9/1977 | Böwing et al. |
| 4,126,573 A | 11/1978 | Johnston |
| 4,170,453 A | 10/1979 | Kitko |
| 4,233,235 A | 11/1980 | Camden et al. |
| 4,367,156 A | 1/1983 | Diehl |
| 4,370,251 A | 1/1983 | Liao et al. |
| 4,412,934 A | 11/1983 | Chung et al. |
| 4,483,778 A | 11/1984 | Thompson et al. |
| 4,486,327 A | 12/1984 | Murphy et al. |
| 4,617,090 A | 10/1986 | Chum et al. |
| 4,655,781 A | 4/1987 | Hsieh et al. |
| 4,681,592 A | 7/1987 | Hardy et al. |
| 4,778,618 A | 10/1988 | Fong et al. |
| 4,853,143 A | 8/1989 | Hardy et al. |
| 4,957,647 A | 9/1990 | Zielske |
| 4,964,870 A | 10/1990 | Fong et al. |
| 5,019,292 A | 5/1991 | Baeck et al. |
| 5,030,240 A | 7/1991 | Wiersema et al. |
| 5,143,641 A | 9/1992 | Nunn |
| 5,196,133 A | 3/1993 | Leslie et al. |
| 5,200,189 A | 4/1993 | Oakes et al. |
| 5,314,687 A | 5/1994 | Oakes et al. |
| 5,431,849 A | 7/1995 | Damhus et al. |
| 5,486,212 A | 1/1996 | Mitchell et al. |
| 5,503,765 A | 4/1996 | Schepers et al. |
| 5,505,740 A | 4/1996 | Kong et al. |
| 5,545,374 A | 8/1996 | French et al. |
| 5,576,282 A | 11/1996 | Miracle et al. |
| 5,595,967 A | 1/1997 | Miracle et al. |
| 5,599,781 A | 2/1997 | Haeggberg et al. |
| 5,637,755 A | 6/1997 | Nagumo et al. |
| 5,681,805 A | 10/1997 | Scheuing et al. |
| 5,716,923 A | 2/1998 | MacBeath |
| 5,718,910 A | 2/1998 | Oakes et al. |
| 5,780,064 A | 7/1998 | Meisters et al. |

(Continued)

FOREIGN PATENT DOCUMENTS

| | | |
|---|---|---|
| DE | 19754290 A1 | 6/1999 |
| EP | 0267047 A2 | 5/1988 |

(Continued)

OTHER PUBLICATIONS

Dannacher, Josef J., "Catalytic bleach: Most valuable applications for smart oxidation chemistry", Journal of Molecular Catalysis A: Chemical 251 (2006) 159-176.

Rusch gen. Klaas, Mark et al., "Biocatalytic peroxy acid formation for disinfection", Journal of Molecular Catalysis B: Enzymatic 19-20 (2002) 499-505.

Rusch gen. Klaas, Mark et al., "Lipase-catalyzed conversions of trimethylsilyl ethers: deprotection, acetylation, epoxidation and one-pot-multi-step reactions", Journal of Molecular Catalysis B: Enzymatic 7 (1999) 283-289.

(Continued)

*Primary Examiner* — Sudhakar Katakam
(74) *Attorney, Agent, or Firm* — McKee, Voorhees & Sease, P.L.C.

(57) ABSTRACT

The present disclosure provides methods for generating percarboxylic acid compositions and/or peroxycarboxylic acid compositions formed external to a point of use in non-equilibrium reactions for use in certain bleaching and antimicrobial applications, in particular laundry applications. The compositions are generated external to a point of use, at alkaline pH levels, viz. greater than about pH 12, and optionally suitable for use with detergents and/or surfactants for synergistic bleaching efficacy. Methods of bleaching and/or disinfecting are further provided.

26 Claims, 1 Drawing Sheet

(56) References Cited

U.S. PATENT DOCUMENTS

| | | |
|---|---|---|
| 5,785,867 A | 7/1998 | LaZonby et al. |
| 5,827,447 A | 10/1998 | Tamura et al. |
| 5,827,808 A | 10/1998 | Appleby et al. |
| 5,880,083 A | 3/1999 | Beaujean et al. |
| 5,977,403 A | 11/1999 | Byers |
| 5,998,350 A | 12/1999 | Burns et al. |
| 6,022,381 A | 2/2000 | Dias et al. |
| 6,110,883 A | 8/2000 | Petri et al. |
| 6,177,393 B1 | 1/2001 | McGregor et al. |
| 6,207,632 B1 | 3/2001 | Brooker et al. |
| 6,221,341 B1 | 4/2001 | Montgomery |
| 6,399,564 B1 | 6/2002 | Speed et al. |
| 6,407,052 B2 | 6/2002 | Gassenmeier et al. |
| 6,417,151 B1 | 7/2002 | Grothus et al. |
| 6,566,318 B2 | 5/2003 | Perkins et al. |
| 6,569,286 B1 | 5/2003 | Withenshaw et al. |
| 6,599,871 B2 | 7/2003 | Smith |
| 6,602,845 B2 | 8/2003 | Connor et al. |
| 6,649,140 B2 | 11/2003 | Paparatto et al. |
| 6,689,732 B1 | 2/2004 | Guedira et al. |
| 6,806,246 B2 | 10/2004 | Preissner et al. |
| 6,878,680 B2 | 4/2005 | Kitko et al. |
| 6,919,304 B2 | 7/2005 | Dykstra et al. |
| 7,012,154 B2 | 3/2006 | Vineyard et al. |
| 7,189,385 B2 | 3/2007 | Montgomery |
| 7,217,295 B2 | 5/2007 | Samain et al. |
| 7,541,324 B2 | 6/2009 | Reinhardt et al. |
| 7,569,232 B2 | 8/2009 | Man et al. |
| 7,569,528 B2 | 8/2009 | Lant et al. |
| 7,598,218 B2 | 10/2009 | Stolte et al. |
| 7,686,892 B2 | 3/2010 | Smets et al. |
| 7,863,234 B2 | 1/2011 | Maki et al. |
| 7,915,445 B2 | 3/2011 | Maatta et al. |
| 7,919,122 B2 | 4/2011 | Okano et al. |
| 2002/0064565 A1 | 5/2002 | Karagoezian |
| 2002/0157189 A1 | 10/2002 | Wang et al. |
| 2003/0100469 A1 | 5/2003 | Connor et al. |
| 2004/0002616 A1 | 1/2004 | Preto et al. |
| 2005/0008526 A1 | 1/2005 | Bianchetti et al. |
| 2005/0109981 A1 | 5/2005 | Tucker et al. |
| 2006/0040847 A1 | 2/2006 | Weibel |
| 2006/0088498 A1 | 4/2006 | Martin et al. |
| 2006/0173209 A1 | 8/2006 | Vineyard et al. |
| 2006/0276366 A1 | 12/2006 | Deljosevic |
| 2007/0042924 A1 | 2/2007 | DiCosimo et al. |
| 2007/0173430 A1 | 7/2007 | Souter et al. |
| 2007/0274857 A1* | 11/2007 | Okano et al. .................. 422/28 |
| 2008/0176784 A1 | 7/2008 | Clowes et al. |
| 2009/0011971 A1 | 1/2009 | Evers |
| 2009/0018049 A1 | 1/2009 | Stolte et al. |
| 2009/0148686 A1 | 6/2009 | Urankar et al. |
| 2009/0175956 A1 | 7/2009 | Buschmann et al. |
| 2009/0249557 A1 | 10/2009 | Maki et al. |
| 2010/0084603 A1 | 4/2010 | Narayan et al. |
| 2010/0227000 A1 | 9/2010 | Ames et al. |
| 2010/0286017 A1 | 11/2010 | Righetto |
| 2010/0308260 A1 | 12/2010 | Maki et al. |
| 2011/0168567 A1 | 7/2011 | Smith et al. |
| 2011/0169270 A1 | 7/2011 | Todorof |
| 2011/0171062 A1 | 7/2011 | Wolfe |
| 2011/0173897 A1 | 7/2011 | Schneider |
| 2011/0177145 A1 | 7/2011 | Erkenbrecher, Jr. et al. |
| 2011/0240510 A1 | 10/2011 | De Poortere et al. |
| 2011/0257060 A1 | 10/2011 | Dykstra |

FOREIGN PATENT DOCUMENTS

| | | |
|---|---|---|
| EP | 384911 A2 | 8/1990 |
| EP | 0751210 A1 | 1/1997 |
| EP | 1010749 A2 | 6/2000 |
| JP | 62155203 A | 7/1987 |
| JP | 5186989 | 7/1993 |
| JP | 6305920 | 11/1994 |
| JP | 2006045146 A | 2/2006 |
| JP | 2006045147 A | 2/2006 |
| WO | 9115474 A1 | 10/1991 |
| WO | 9403395 A1 | 2/1994 |
| WO | 9410284 A1 | 5/1994 |
| WO | 9418299 A1 | 8/1994 |
| WO | 9424869 A1 | 11/1994 |
| WO | 9429509 A1 | 12/1994 |
| WO | 9502030 A1 | 1/1995 |
| WO | 9521290 A1 | 8/1995 |
| WO | 9614384 A1 | 5/1996 |
| WO | 9616148 A1 | 5/1996 |
| WO | 9743393 A2 | 11/1997 |
| WO | 9803513 A1 | 1/1998 |
| WO | 9811189 A1 | 3/1998 |
| WO | 9818893 A1 | 5/1998 |
| WO | 9931215 A1 | 6/1999 |
| WO | 9932598 A1 | 7/1999 |
| WO | 0042145 A1 | 7/2000 |
| WO | 0078911 A1 | 12/2000 |
| WO | 03050343 A2 | 6/2003 |
| WO | 2006016145 A1 | 2/2006 |
| WO | 2006094232 A1 | 9/2006 |
| WO | 2006131503 A2 | 12/2006 |
| WO | 2010050634 A1 | 5/2010 |

OTHER PUBLICATIONS

Tsunokawa, Youko et al., "A Versatile Method for Preparation of O-Alkylperoxycarbonic Acids: Epoxidation with Alkyloxycarbonylimidazoles and Hydrogen Peroxide", Tetrahedron Letters, vol. 23, No. 20, (1982), pp. 2113-2116.

Yin, De Lu (Tyler), et al., "switching Catalysis from Hydrolysis to Perhydrolysis in *Pseudomonas fluorescens* Esterase", Biochemistry, (2010), 49, 1931-1942.

ECOLAB USA, Inc. et al., PCT/IB2011/055830 filed Dec. 20, 2011, "Notification of Transmittal of the International Search Report and the Written Opinion of the International Searching Authority, or the Declaration" mailed Aug. 24, 2012, 8 pages.

ECOLAB USA, Inc. et al., PCT/IB2011/055832 filed Dec. 20, 2011, "Notification of Transmittal of the International Search Report and the Written Opinion of the International Searching Authority, or the Declaration" mailed Aug. 14, 2012, 14 pages.

English Abstract of JP62155203, published on Jul. 10, 1987 (1 page).

English Abstract of JP6305920, published on Nov. 1, 1994 (1 page).

Caboni-Oerlemans, Chiara, et al., "Hydrolase-catalysed synthesis of peroxycarboxylic acids: Biocatalytic promiscuity for practical applications", Elsevier, Journal of Biotechnology, 126 (2006) 140-151 (12 pages).

Effkemann, Stefan, et al., "Peroxide analysis in laundry detergents using liquid chromotography", Elsevier, Analytica Chimica Acta, 363 (1998) 97-103 (7 pages).

Leveneur, Sébastien, "Synthesis of peroxypropionic acid from propionic acid and hydrogen peroxide over heterogeneous catalysts", Elsevier, Chemical Engineering Journal, 147 (2009) 323-329 (7 pages).

Maeda, Hatsuo, et al., "Assessment of Acyl Groups and Reaction Conditions in the Competition between Perhydrolysis and Hydrolysis of Acyl Resorufins for Developing an Indicator Reaction for Fluorometric Analysis of Hydrogen Peroxide", Pharmaceutical Society of Japan, Cehm. Pharm. Bull. 50(2) 169-174, 2002 (6 pages).

Muurinene, Esa, "Organosolv Pulping—A review and distillation study related to peroxyacid pulping", Department of Process Engineering, University of Oulu, May 16, 2000, Oulu, Finland (314 pages).

Ogata, Y., et al., "The Formation of Peracids by the Perhydrolysis With Alkaline Hydrogen Peroxide", Tetrochem, vol. 23, pp. 3327-3332, Pergamom Press, 1967 (7 pages).

Rusch gen. Klaas, Mark, et al., "Lipase-catalyzed preparation of peroxy acids and their use for expoxidation", Elsevier, Journal of Molecular Catalysis A: Chemical 117 (1997) 311-319 (9 pages).

English Translation of JP2006045146A, published Feb. 16, 2006 (14 pages).

(56) References Cited

OTHER PUBLICATIONS

English Translation of JP2006045147A, published Feb. 16, 2006 (16 pages).
Brooks, Robert E., et al., "Alkaline hydrogen peroxide bleaching of cellulose", Kluwer Academic Publishers, Cellulose 7: 263-286, 2000 (24 pages).
Chen, J., "Enhanced Alkaline Peroxide Bleaching of Softwood Kraft Pulps Using a New Activator," Journal of Pulp and Paper Science: vol. 27, No. 12, Dec. 2001 (4 pages).
Lee, Jung Jin, et al., "Hydrolytic stability of a series of lactam-based cationic bleach activators and their impact on cellulose peroxide bleaching", Springer Science+Business Medica B.V., Cellulose (2010) 17:671-678 (8 pages).

* cited by examiner

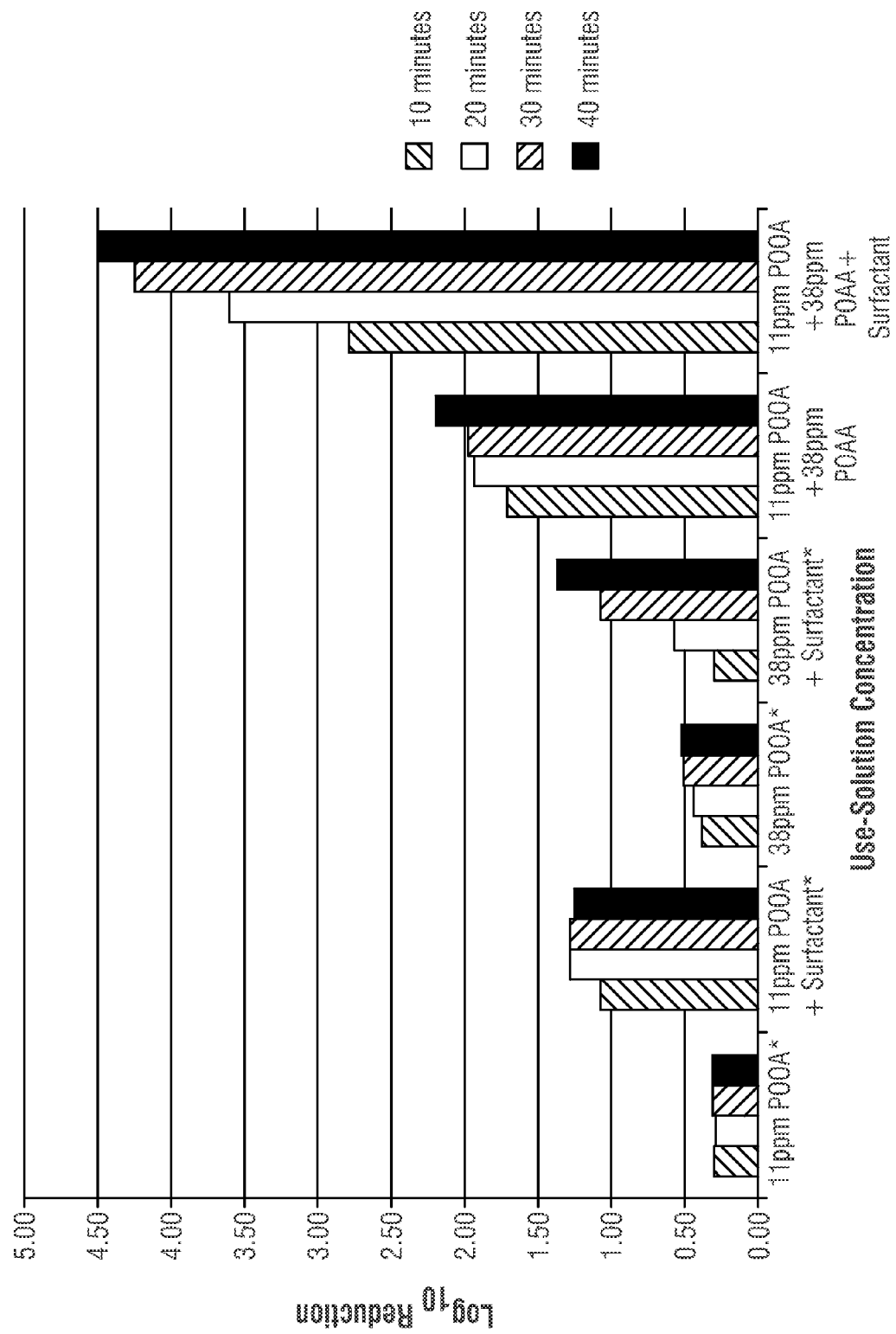

GENERATION OF PEROXYCARBOXYLIC ACIDS AT ALKALINE PH, AND THEIR USE AS TEXTILE BLEACHING AND ANTIMICROBIAL AGENTS

CROSS REFERENCE TO RELATED APPLICATIONS

This application is a continuation-in-part of U.S. Provisional Application No. 61/427,951, filed Dec. 29, 2010, entitled Sugar Ester Peracid On-Site Generator and Formulator, and U.S. Provisional Application No. 61/427,965, filed Dec. 29, 2010, entitled In Situ Generation of Peroxycarboxylic Acids at Alkaline pH, and Methods of Use Thereof, each of which are herein incorporated by reference in their entirety.

This application is related to U.S. patent application Publication Nos. U.S. 2012/0172440 and U.S. 2012/0172441, entitled In Situ Generation of Peroxycarboxylic Acids at Alkaline pH and Methods of Use Thereof, U.S. Patent Application Publication No. U.S. 2012/0322872, entitled Sugar Ester Peracid On-Site Generator and Formulator, U.S. Patent Application Publication No. U.S. 2012/0172437, entitled Continuous On-Line Adjustable Disinfectant/Sanitizer/Bleach Generator, and U.S. Patent Application Publication No. U.S. 2012/0171076, entitled Water Temperature as a Means of Controlling Kinetics of Onsite Generated Peracids, each filed concurrently herewith. The entire contents of these patent applications are hereby expressly incorporated herein by reference including, without limitation, the specification, claims and abstract, as well as any figures, tables or drawings thereof.

FIELD OF THE INVENTION

The present disclosure relates to methods for bleaching and antimicrobial use of peroxycarboxylic acid compositions generated external to a point of use, at alkaline pH levels, viz. greater than about pH 12. The present disclosure also relates to methods for bleaching and antimicrobial use of mixed percarboxylic acid compositions generated external to a point of use, at alkaline pH levels.

BACKGROUND OF THE INVENTION

Peroxycarboxylic acids are known for use as antimicrobials and bleaching agents. Mixed peroxycarboxylic acid systems are also known for use as antimicrobial and bleaching agents. However, there are disadvantages to use of these antimicrobial and bleaching agents. For example, the most commonly used peroxycarboxylic acid, peroxyacetic acid, is known to have a strong pungent odor. In addition, peracids (e.g. peroxyacids) such as peroxycarboxylic acid have known chemical disadvantages, namely, they are relatively instable in solution and decompose to ordinary oxyacids and oxygen.

Conventional peroxycarboxylic acid compositions are made through an acid catalyzed equilibrium reaction. Most often, the peroxycarboxylic acids are generated in a chemical plant, and then shipped to customers for on-site use. Due to the limited storage stability of peroxycarboxylic acids, the peroxycarboxylic acids must be packed in special containers and shipped under the strict Department of Transportation (DOT) guidelines. Certain improvements to peroxycarboxylic acid stability have proved advantageous for shipping purposes, as described in U.S. patent application Ser. No. 11/847,604, entitled "Shelf Stable, Reduced Corrosion, Ready to Use Peroxycarboxylic Acid Antimicrobial Compositions," the entire contents of which are hereby expressly incorporated herein by reference. Most commercially available products in an equilibrium mixture contain excess hydrogen peroxide in the presence of stabilizers and acid catalysts, to stabilize and improve the composition's shelf life. Despite stability improvements, excess amounts of reagents (e.g., acids, oxidizing agents, and stabilizers) are present in the compositions to help form the desired amount of peracids and to prevent decomposition during shipping and storage. These and other disadvantages to the use of equilibrium peracid compositions exist.

Bleach activators are organic compounds with at least one reactive acyl group together with a leaving group. When reacted with a perhydroxyl anion, bleach activators yield an organic peracid in situ. Conventionally this means within a washing machine, whether washer-extractor or continuous batch, i.e. tunnel, washer. Bleach activators have been used to activate peroxygen bleaches, such as hydrogen peroxide, to improve stain removal at lower wash temperatures.

Traditional bleach activators suffer from several limitations. Because the reaction between the activator and the perhydroxyl anion takes place in the dilute wash bath, both the rate and extent of reaction are reduced compared to if the washing solution were more concentrated. Furthermore, the bleach activator must balance between a highly alkaline pH that promotes rapid perhydrolysis and a less alkaline pH where the formed peracid is most effective. It is known that peracids give optimal bleaching close to their pKa value (e.g. pKa 8.2 for peroxyacetic acid). However, conventional bleach activators will exhibit very little perhydrolysis at that low pH. To balance those objectives, a pH value of about 10 is conventionally used for bleach activators, though it is not the optimal point for peracid formation nor peracid performance. Given those limitations, there remains a need for bleach activator system which, by increasing both the concentration and pH, can generate peracids more efficiently. One such method is the on-site generation of peracid compositions that can be generated ex situ to a washing application, such as a washing machine or tunnel washer, at both higher concentration and pH, and then transferred to a washing vessel where the peracid can perform at a lower pH and may optionally be combined in situ with detergents and/or surfactants for synergistic efficacy.

Accordingly, it is an objective of the claimed invention to generate peroxycarboxylic acids and mixed percarboxylic acids on site under alkaline pH for textile bleaching and antimicrobial activity.

It is a further objective of the claimed invention to develop methods of rapidly generating peroxycarboxylic acids and mixed percarboxylic acids at alkaline pH for bleaching applications, including for example textile care. A further object of the invention is to develop methods of rapidly generating peroxycarboxylic acids and mixed percarboxylic acids at alkaline pH for antimicrobial applications, including for example health care and other applications.

A further object of the invention is to utilize on-site methods and/or apparatus for generating stable single and/or mixed peracid and/or peroxyacid systems for use with detergents and/or surfactants for synergistic efficacy.

BRIEF SUMMARY OF THE INVENTION

In some aspects, the present disclosure relates to a method for forming a single percarboxylic acid composition for bleaching and antimicrobial activity and/or sanitizing and/or disinfecting applications comprising (a) providing a reaction mixture comprising: (i) at least one ester of a polyhydric alcohol and a C1 to C18 carboxylic acid; (ii) a source of alkalinity; and (iii) an oxidizing agent, wherein the reaction mixture has a pH greater than about 12, is not at equilibrium, and is substantially free of a stabilizing agent; (b) allowing the reaction mixture to react for a sufficient amount of time such that at least one C1 to C18 percarboxylic acid is generated to form a peroxycarboxylic acid composition ex situ from said bleaching and disinfecting application; and (c) optionally providing said bleaching and antimicrobial activity and/or sanitizing and/or disinfecting composition with a surfactant source for synergistic bleaching and disinfectant efficacy at a point of use.

In other aspects, the present disclosure relates to a method for forming a mixed percarboxylic acid composition comprising (a) providing a reaction mixture comprising: (i) a first ester of a polyhydric alcohol and a C1 to C18 carboxylic acid; (ii) a source of alkalinity; and (iii) an oxidizing agent; (b) allowing the reaction mixture to react for a sufficient amount of time, and then adding a second ester of a polyhydric alcohol and a C1 to C18; (c) after addition of the second ester allowing the mixture to react for a sufficient amount of time such that a mixed peroxycarboxylic acid composition forms said bleaching and antimicrobial activity and/or sanitizing and/or disinfecting composition ex situ from said bleaching and antimicrobial activity and/or sanitizing and/or disinfecting application; wherein the reaction mixture has a pH greater than about 12, is not at equilibrium, and is substantially free of a stabilizing agent; and (d) optionally providing said bleaching and antimicrobial activity and/or sanitizing and/or disinfecting composition with a surfactant source for synergistic bleaching and disinfectant efficacy at a point of use.

According to the various aspects of the invention, the methods of making the single and/or mixed percarboxylic acid compositions for bleaching and antimicrobial activity and/or sanitizing and/or disinfecting applications occur at an alkaline pH ex situ to a point of use and combination with a surfactant and/or detergent source for bleaching and antimicrobial activity and/or sanitizing and/or disinfecting. The methods of making the compositions may include any of the embodiments of the invention disclosed herein, including the use of various reagents sourced as either individual reagents and/or using a variety of concentrated premix formulations. In some aspects, the reaction mixture is comprised of (i) a first reagent premix comprising said ester of a polyhydric alcohol and a C1 to C18 carboxylic acid and said oxidizing agent, and (ii) a second reagent source comprising said source of alkalinity, wherein said reagent premix further comprises at least one reagent selected from the group consisting of a dispersing agent, a solvent, water and mixtures thereof.

In other aspects, the present disclosure relates to methods for bleaching and/or antimicrobial activity and/or sanitizing and/or disinfecting a surface comprising: (a) forming a single or mixed peroxycarboxylic acid bleaching and antimicrobial activity and/or sanitizing and/or disinfecting composition ex situ from a point of use by reacting a composition comprising at least one ester of a polyhydric alcohol and a C1 to C18 carboxylic acid, a source of alkalinity, and an oxidizing agent; and (b) providing a surfactant source for synergistic bleaching and disinfectant efficacy with said ex situ generated peroxycarboxylic acid bleaching and antimicrobial activity and/or sanitizing and/or disinfecting composition; and (c) contacting said surface at a point of use with said peroxycarboxylic acid bleaching and antimicrobial activity and/or sanitizing and/or disinfecting composition and said surfactant source.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

BRIEF DESCRIPTION OF DRAWINGS

FIG. 1 shows a graphical illustration of the log reductions of *C. difficile* spores for different test substances at varying contact times demonstrating the efficacy of the claimed invention.

Various embodiments of the present invention will be described in detail with reference to the drawings, wherein like reference numerals represent like parts throughout the several views. Reference to various embodiments does not limit the scope of the invention. Figures represented herein are not limitations to the various embodiments according to the invention and are presented for exemplary illustration of the invention.

DETAILED DESCRIPTION OF THE INVENTION

The present disclosure relates to peroxycarboxylic acid compositions generated ex situ for bleaching and/or antimicrobial activity and/or sanitizing and/or disinfecting applications of use. In particular, the present invention uses methods for generating peroxycarboxylic acid compositions from a non-equilibrium ester based reaction, as well as methods of making and using such compositions. The compositions disclosed herein have many advantages over conventional, equilibrium based peroxycarboxylic acid compositions. For example, after peroxycarboxylic acid formation according to methods disclosed herein, the compositions have significantly lower levels of reactants compared to peroxycarboxylic acid compositions generated using equilibrium reactions along with greater amounts of reacted peroxycarboxylic acid and less unreacted reagent residues compared to peroxycarboxylic acid compositions generated using equilibrium reactions. Further, as the compositions are generated on site for a particular bleaching and/or antimicrobial activity and/or sanitizing and/or disinfecting application, therefore the compositions can be substantially free of, or even free of, stabilizers. Additionally, due to the ability to generate the disclosed peroxycarboxylic acid compositions on site, the step of shipping hazardous peroxycarboxylic acid compositions to an end user can be eliminated. The on-site generated peroxycarboxylic acid compositions according to the invention may optionally be combined with surfactants for additional synergy in bleaching and/or antimicrobial activity and/or sanitizing and/or disinfecting efficacy. Notably, when used the surfactant is added after the generation of the peroxycarboxylic acid compositions (e.g. down the line, such as a tunnel washing method) for the boosting of antimicrobial efficacy and bleaching efficacy (e.g. synergistic results are achieved). These and other benefits of the present invention are disclosed herein.

The embodiments of this invention are not limited to particular peroxycarboxylic acid compositions and methods for on-site generation of the same, which can vary and are understood by skilled artisans. It is further to be understood that all terminology used herein is for the purpose of describing particular embodiments only, and is not intended to be limiting in any manner or scope. For example, as used in this specification and the appended claims, the singular forms "a," "an" and "the" can include plural referents unless the content clearly indicates otherwise. Further, all units, prefixes, and symbols may be denoted in its SI accepted form. Numeric ranges recited within the specification are inclusive of the numbers defining the range and include each integer within the defined range.

Definitions

So that the present invention may be more readily understood, certain terms are first defined. Unless defined otherwise, all technical and scientific terms used herein have the same meaning as commonly understood by one of ordinary skill in the art to which embodiments of the invention pertain. Many methods and materials similar, modified, or equivalent to those described herein can be used in the practice of the embodiments of the present invention without undue experimentation, the preferred materials and methods are described herein. In describing and claiming the embodiments of the present invention, the following terminology will be used in accordance with the definitions set out below.

As used herein, the term "about" refers to variation in the numerical quantity that can occur, for example, through typical measuring and liquid handling procedures used for making concentrates or use solutions in the real world; through inadvertent error in these procedures; through differences in the manufacture, source, or purity of the ingredients used to make the compositions or carry out the methods; and the like. The term "about" also encompasses amounts that differ due to different equilibrium conditions for a composition resulting from a particular initial mixture. Whether or not modified by the term "about", the claims include equivalents to the quantities.

As used herein, the term "alkyl" or "alkyl groups" refers to saturated hydrocarbons having one or more carbon atoms, including straight-chain alkyl groups (e.g., methyl, ethyl, propyl, butyl, pentyl, hexyl, heptyl, octyl, nonyl, decyl, etc.), cyclic alkyl groups (or "cycloalkyl" or "alicyclic" or "carbocyclic" groups) (e.g., cyclopropyl, cyclopentyl, cyclohexyl, cycloheptyl, cyclooctyl, etc.), branched-chain alkyl groups (e.g., isopropyl, tert-butyl, sec-butyl, isobutyl, etc.), and alkyl-substituted alkyl groups (e.g., alkyl-substituted cycloalkyl groups and cycloalkyl-substituted alkyl groups).

Unless otherwise specified, the term "alkyl" includes both "unsubstituted alkyls" and "substituted alkyls." As used herein, the term "substituted alkyls" refers to alkyl groups having substituents replacing one or more hydrogens on one or more carbons of the hydrocarbon backbone. Such substituents may include, for example, alkenyl, alkynyl, halogeno, hydroxyl, alkylcarbonyloxy, arylcarbonyloxy, alkoxycarbonyloxy, aryloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), imino, sulfhydryl, alkylthio, arylthio, thiocarboxylate, sulfates, alkylsulfinyl, sulfonates, sulfamoyl, sulfonamido, nitro, trifluoromethyl, cyano, azido, heterocyclic, alkylaryl, or aromatic (including heteroaromatic) groups.

In some embodiments, substituted alkyls can include a heterocyclic group. As used herein, the term "heterocyclic group" includes closed ring structures analogous to carbocyclic groups in which one or more of the carbon atoms in the ring is an element other than carbon, for example, nitrogen, sulfur or oxygen. Heterocyclic groups may be saturated or unsaturated. Exemplary heterocyclic groups include, but are not limited to, aziridine, ethylene oxide (epoxides, oxiranes), thiirane (episulfides), dioxirane, azetidine, oxetane, thietane, dioxetane, dithietane, dithiete, azolidine, pyrrolidine, pyrroline, oxolane, dihydrofuran, and furan.

The term "cleaning," as used herein, means to perform or aid in soil removal, bleaching, microbial population reduction, or combination thereof.

For the purpose of this patent application, successful microbial reduction is achieved when the microbial populations are reduced by at least about 50%, or by significantly more than is achieved by a wash with water. Larger reductions in microbial population provide greater levels of protection.

As used herein, the term "disinfectant" refers to an agent that kills all vegetative cells including most recognized pathogenic microorganisms, according to an applicable standard for laundry and/or other soft surface treatments. The definition of disinfectant for hard surfaces often refers to the procedure described in *A.O.A.C. Use Dilution Methods,* Official Methods of Analysis of the Association of Official Analytical Chemists, paragraph 955.14 and applicable sections, 15th Edition, 1990 (EPA Guideline 91-2). According to the invention these definitions may require adaptation for laundry and/or other soft surface applications as opposed to hard surface treatments. As used herein, the term "high level disinfection" or "high level disinfectant" refers to a compound or composition that kills substantially all organisms, except high levels of bacterial spores, and is effected with a chemical germicide cleared for marketing as a sterilant by the Food and Drug Administration. As used herein, the term "intermediate-level disinfection" or "intermediate level disinfectant" refers to a compound or composition that kills mycobacteria, most viruses, and bacteria with a chemical germicide registered as a tuberculocide by the Environmental Protection Agency (EPA). As used herein, the term "low-level disinfection" or "low level disinfectant" refers to a compound or composition that kills some viruses and bacteria with a chemical germicide registered as a hospital disinfectant by the EPA.

As used herein, the term "fouling" shall be understood to mean the undesirable presence of or any deposition of any organic or inorganic material in the applicable composition or chemistry.

As used herein, the term "free" or "substantially free" refers to a composition, mixture, or ingredient that does not contain a particular compound or to which a particular compound or a particular compound-containing compound has not been added. Should the particular compound be present through contamination and/or use in a minimal amount of a composition, mixture, or ingredients, the amount of the compound shall be less than about 3 wt-%. More preferably, the amount of the compound is less than 2 wt-%, less than 1 wt-%, and most preferably the amount of the compound is less than 0.5 wt-%.

As used herein, the term "laundry" refers to items or articles that are cleaned in a laundry washing machine. In general, laundry refers to any item or article made from or including textile materials, woven fabrics, non-woven fabrics, and knitted fabrics. The textile materials can include natural or synthetic fibers such as silk fibers, linen fibers, cotton fibers, polyester fibers, polyamide fibers such as nylon, acrylic fibers, acetate fibers, and blends thereof including cotton and polyester blends. The fibers can be treated or untreated.

As used herein, the term "microorganism" refers to any noncellular or unicellular (including colonial) organism. Microorganisms include all prokaryotes. Microorganisms include bacteria (including cyanobacteria), spores, lichens, fungi, protozoa, virinos, viroids, viruses, phages, and some algae. As used herein, the term "microbe" is synonymous with microorganism.

As used herein, the terms "mixed" or "mixture" when used relating to "peroxycarboxylic acid composition" or "peroxycarboxylic acids" refer to a composition or mixture including more than one peroxycarboxylic acid, such as a composition or mixture including peroxyacetic acid (POAA) and peroxyoctanoic acid (POOA).

As used herein, the terms "mixed," "mixture" or "more than one" when used relating to esters suitable for use in forming the compositions of the invention refer to a composition or mixture including more than one ester group undergoing a perhydrolysis reaction to form the peroxycarboxylic composition. The use of at least one ester of a polyhydric alcohol and a C1 to C18 carboxylic acid according to the invention includes the use of various forms of the ester, such as the mono, di, tri and/or mixtures thereof formations of the particular ester. Accordingly, examples of suitable forms of esters for use as "mixtures" or comprising "more than one" include, but are not limited to, glycerol monooctanoate, glycerol dioctanoate, glycerol trioctanoate, sorbitan monooctanoate, sorbitan dioctanoate, sorbitan trioctanoate, and mixtures and derivatives thereof. Further, as one skilled in the art shall ascertain based upon the description of the invention disclosed herein, the use of an ester source, such as glycerol octanoate, may further comprise the use of the mono, di and tri esters and/or mixtures thereof. According to various embodiments of the invention, the use of "an" ester, such as octanoic glyceride, may include the use of a "mixture" of esters wherein more than one formation of the ester is present, including for example the mono, di and tri formations and/or mixtures thereof.

As used herein, the phrases "objectionable odor," "offensive odor," or "malodor," refer to a sharp, pungent, or acrid odor or atmospheric environment from which a typical person withdraws if they are able to. Hedonic tone provides a measure of the degree to which an odor is pleasant or unpleasant. An "objectionable odor," "offensive odor," or "malodor" has an hedonic tone rating it as unpleasant as or more unpleasant than a solution of 5 wt-% acetic acid, propionic acid, butyric acid, or mixtures thereof.

As used herein, the terms "peracid" or "peroxy acid" refer to an acid having the hydrogen of the hydroxyl group replaced by a hydroxy group. Oxidizing peracids are referred to herein as peroxycarboxylic acids.

As used herein, the term "polyhydric alcohol" or "polyol," refers to an alcohol that has two or more hydroxyl groups. Polyhydric alcohols suitable for use in the compositions include, but are not limited to, sugars, sugar alcohols, and mixtures and derivatives thereof.

As used herein, the term "sanitizer" refers to an agent that reduces the number of bacterial contaminants to safe levels. According to an embodiment the reduction may be judged by public health requirements, such as applicable standards for reduction of bacterial levels in laundry and/or other soft surface applications. In an embodiment, sanitizers for use in this invention will provide at least a 99.999% reduction (5-log order reduction). These reductions can be evaluated using a procedure set out in *Germicidal and Detergent Sanitizing Action of Disinfectants*, Official Methods of Analysis of the Association of Official Analytical Chemists, paragraph 960.09 and applicable sections, 15th Edition, 1990 (EPA Guideline 91-2), with adaptation for the use in laundry applications as opposed to hard surface treatments. According to this reference a hard surface sanitizer should provide a 99.999% reduction (5-log order reduction) within 30 seconds at room temperature, 25±2° C., against several test organisms.

As used in this invention, the term "sporicide" refers to a physical or chemical agent or process having the ability to cause greater than a 90% reduction (1-log order reduction) in the population of spores of *Bacillus cereus* or *Bacillus subtilis* within 10 seconds at 60° C. In certain embodiments, the sporicidal compositions of the invention provide greater than a 99% reduction (2-log order reduction), greater than a 99.99% reduction (4-log order reduction), or greater than a 99.999% reduction (5-log order reduction) in such population within 10 seconds at 60° C. For purposes of the present invention, a sporicide is provides the same levels of reduction in the population of spores under conditions for laundry and/or other soft surface applications as opposed to hard surface treatments.

Differentiation of antimicrobial "-cidal" or "-static" activity, the definitions which describe the degree of efficacy, and the official laboratory protocols for measuring this efficacy are considerations for understanding the relevance of antimicrobial agents and compositions. Antimicrobial compositions can affect two kinds of microbial cell damage. The first is a lethal, irreversible action resulting in complete microbial cell destruction or incapacitation. The second type of cell damage is reversible, such that if the organism is rendered free of the agent, it can again multiply. The former is termed microbiocidal and the later, microbistatic. A sanitizer and a disinfectant are, by definition, agents which provide antimicrobial or microbiocidal activity. In contrast, a preservative is generally described as an inhibitor or microbistatic composition As used herein the term "sugar" refers to carbohydrates including one, two, or more saccharose groups. Sugars are a group of organic compounds related by molecular structure that comprise simpler members of the general class of carbohydrates. Each sugar consists of a chain of 2 to 7 carbon atoms (usually 5 or 6). Sugars have the general formula $C_nH_{2n}O_n$, wherein n is between 2 and 7. One of the carbons carries aldehydic or ketonic oxygen which may be combined in acetal or ketal forms and the remaining carbon atoms usually bear hydrogen atoms and hydroxyl groups. In general, sugars are more or less sweet, water soluble, colorless, odorless, optically active substances which lose water, caramelize and char when heated. Exemplary sugars include, but are not limited to, glucose, sucrose, lactose and mixtures thereof.

As used herein, the term "sugar alcohol" refers to the hydrogenated form of a carbohydrate, wherein the carbonyl group of the carbohydrate has been reduced to a primary or secondary hydroxyl group. Sugar alcohols have the general formula $CH_2OH(CHOH)_nCH_2OH$, wherein n is from 2 to 5. Exemplary sugar alcohols include, but are not limited to, glycol, ethylene glycol, propylene glycol, glycerol, erythritol, pentaerythritol, threitol, arabitol, xylitol, ribitol, mannitol, sorbitol, sorbitan, dulcitol, iditol, inositol, isomalt, maltitol, lactitol, polyglycitol, 1,4-cyclohexane diol, and mixtures and derivatives thereof. In some embodiments, the sugar alcohol is selected from ethylene glycol, propylene glycol, glycerol, polyglycerol, sorbitol, sorbitan, and mixtures and derivatives thereof.

As used herein, the term "waters" includes food process or transport waters. Food process or transport waters include produce transport waters (e.g., as found in flumes, pipe transports, cutters, slicers, blanchers, retort systems, washers, and the like), belt sprays for food transport lines, boot and handwash dip-pans, third-sink rinse waters, and the like. Waters also include domestic and recreational waters such as pools, spas, recreational flumes and water slides, fountains, and the like.

As used herein, "weight percent," "wt-%," "percent by weight," "% by weight," and variations thereof refer to the concentration of a substance as the weight of that substance divided by the total weight of the composition and multiplied by 100. It is understood that, as used here, "percent," "%," and the like are intended to be synonymous with "weight percent," "wt-%," etc.

It should be noted that, as used in this specification and the appended claims, the singular forms "a," "an," and "the" include plural referents unless the content clearly dictates otherwise. Thus, for example, reference to a composition containing "a compound" includes a composition having two or more compounds. It should also be noted that the term "or" is generally employed in its sense including "and/or" unless the content clearly dictates otherwise.

Embodiments of the Invention

In some aspects, the present disclosure relates to generating a non-equilibrium or stoichiometric peroxycarboxylic acid forming compositions (also referred to as a peroxycarboxylic acid compositions) for use in various textile bleaching and/or antimicrobial activity and/or sanitizing and/or disinfecting, optionally using the synergy of such compositions with surfactants. Methods of using the peroxycarboxylic acid compositions for various applications including textile bleaching and/or antimicrobial activity and/or sanitizing and/or disinfecting in combined use with surfactants are also disclosed.

Peroxycarboxylic acids are known for use as antimicrobials and bleaching agents. Conventional peroxycarboxylic acid compositions are formed through an acid catalyzed equilibrium reaction. Although acid catalyzed equilibrium reactions are commonly used to generate peroxycarboxylic acids, there are many downsides to such compositions, including, but not limited to the use of excess amounts of reactants required to drive the equilibrium reaction, along with the hazardous shipping conditions required to provide a customer the peroxycarboxylic acid compositions. The present methods of forming the peroxycarboxylic acid compositions suitable for synergistic use with surfactants for bleaching and/or antimicrobial activity and/or sanitizing and/or disinfecting according to the invention avoid these issues.

While an understanding of the mechanism is not necessary to practice the present invention and while the present invention is not limited to any particular mechanism of action, it is contemplated that, in some embodiments the benefits afforded according to the invention result from the production of a non-equilibrium chemistry. Beneficially, the reacted peracids according to the invention are obtained in greater amounts than in equilibrium chemistry wherein greater amounts of unreacted hydrogen peroxide and other reagents would be present. According to the present invention, an aqueous solution of the peroxycarboxylic acid(s) produced contains a relatively higher concentration of peroxycarboxylic acid(s) compared to unreacted hydrogen peroxide component. This is significantly advantageous for the antimicrobial, disinfectant, bleaching and other cleaning applications disclosed herein as desirable according to the embodiments of the invention.

In some aspects, the methods of the invention generate peracid from about 0.25% to about 20%. In some aspects, the methods of the invention generate peracid of about 2%, at least about 3%, preferably at least about 4%, more preferably at least about 5%, and still most preferably at least about 6% peracid from the reaction mixtures (reagents) according to the invention, namely the reaction of an ester or a mixture of esters of a polyhydric alcohol and a C1 to C18 carboxylic acid, a source of alkalinity, an oxidizing agent, and optionally an acidulating agent. Rather than providing a peracid composition in an equilibrium mixture, on site generation of the peracid composition allows the peracids to be produced stoichiometrically through selecting the composition of the starting materials. The on-site systems according to the invention therefore generate higher concentrations of the peroxycarboxylic acid(s) than are available in equilibrium systems. In particular, according to the invention the systems generate higher concentrations of the peroxycarboxylic acid(s) and lower concentrations of hydrogen peroxide (e.g. unreacted reagents) than achieved in equilibrium systems. In addition, the methods of the present invention generate peroxycarboxylic acid(s) under alkaline conditions. Optionally, the alkaline solutions can thereafter be adjusted to acidic conditions to stabilize the peroxycarboxylic acid(s) and ensure the peroxycarboxylic acid(s) compositions do not disassociate, thereby providing stability for a sufficient amount of time to allow the use of the compositions on site after generation, preferably within a matter of hours or days. As disclosed according to the invention, various methods of use disclosed herein do not require the acidification of the compositions.

As referred to herein, peroxycarboxylic acid forming compositions according to the invention refer to the generation of peroxycarboxylic acids ex situ to the point of application (e.g. washer-extractor or tunnel washer), in a non-equilibrium reaction. In particular embodiments of the invention, the methods produce the conjugate base of the peracid which will be protonated to the peroxycarboxylic acid upon acidification. According to additional aspects of the invention, the methods may produce peroxycarboxylic acid compositions upon acidification.

Compositions

In some aspects, the present disclosure relates to peroxycarboxylic acid forming compositions. That is, the compositions are capable of generating peroxycarboxylic acids on site, in a non-equilibrium reaction. Surprisingly, it has been found that peroxycarboxylic acid compositions can be formed at relatively high pH levels, viz. pH greater than about 12, or pH greater than about 13. It has also been found that mixed peroxycarboxylic acid compositions, viz. compositions that form two or more peroxycarboxylic acids, can be generated on site in accordance with the methods disclosed herein. Peroxycarboxylic (or percarboxylic) acids generally have the formula $R(CO_3H)n$, where, for example, R is an alkyl, aryl alkyl, cycloalkyl, aromatic, or heterocyclic group, and n is one, two, or three, and named by prefixing the parent acid with peroxy. The R group can be saturated or unsaturated as well as substituted or unsubstituted.

In an embodiment of the invention the peroxycarboxylic acid forming compositions comprise individual reagents combined according to the invention. These reagents are described herein individually along and include at least one ester of a polyhydric alcohol and a C1 to C18 carboxylic acid, an oxidizing agent, a source of alkalinity, solvents, and other functional groups. An acidulant is also described herein as a reagent that may optionally be added to the compositions. Alternatively, there may be benefits to providing the reagents in various premix formulations to decrease the number of reagents and/or increase the simplicity of the invention. Each of these embodiments, including the peroxycarboxylic acid compositions, are described in further detail in related applications Publication Nos. U.S. 2012/0172440 and U.S. 2012/0172441, entitled In Situ Generation of Peroxycarboxylic Acids at Alkaline pH and Methods of Use Thereof, incorporated herein by reference in its entirety.

In addition to the disclosure relating to the reagents and/or concentrated premixes suitable for use according to the invention, various embodiments of the premix formulations are particularly well suited for use according to the present invention. In a particular aspect, a concentrated premix formulation comprises at least one ester of a polyhydric alcohol and a carboxylic acid, oxidizing agent and a solvent.

According to an embodiment of the invention, the use of a solvent (e.g. methanol) promotes the use of various ester mixtures. As the selection of the various forms of an ester is impacted by the water solubility of the compositions, the use of a solvent to enhance water solubility of the composition will provide benefits for compositions using a mixture of esters, namely the less soluble ester form (e.g. tri-formations). Solvents suitable for the concentrated premix formulations according to the invention include, for example, organic solvents such as alcohol, ether or ketone. Preferably, the solvent is a water soluble alcohol, such as ethanol or methanol.

According to a preferred embodiment of the invention, a concentrated premix formulation may comprise, consist of and/or consist essentially of at least one ester of a polyhydric alcohol and a carboxylic acid, hydrogen peroxide and a water soluble alcohol solvent. More preferably, the concentrated premix formulation may comprise, consist of and/or consist essentially of glycerol octanoate and/or other ester sources according to the invention, hydrogen peroxide and ethanol. According to an embodiment of the invention, the concentrated premix formulation is thereafter combined with the source of alkalinity and water to form the peroxycarboxylic acid composition of the invention.

These and other reagents and/or concentrated premix formulations may be used according to the invention described herein.

Methods for Making Using Individual Reagents

In some aspects, the present disclosure provides methods for making the peroxycarboxylic acid compositions disclosed herein. The method includes combining at least one ester of a polyhydric alcohol and a C1 to C18 carboxylic acid, a source of alkalinity and an oxidizing agent. This reaction mixture allows for the perhydrolysis of the ester to form the corresponding C1 to C18 peroxycarboxylic acid. Without wishing to be bound by any particular theory it is thought that the oxidizing agent present perhydrolyzes the ester bonds, thereby forming the corresponding percarboxylic acids.

In some embodiments, the pH of the reaction mixture is greater than about 12. In other embodiments, the reaction mixture is greater than about 12.5, or greater than about 13. The reagents can be combined in any suitable manner. Exemplary systems and methods for making the compositions are described in further detail in U.S. patent application Ser. No. 61/427,951 and Publication No. U.S. 2012/03228721, entitled Sugar Ester Peracid On-Site Generator and Formulator, U.S. Patent Application Publication No. U.S. 2012/0172437, entitled Continuous On-Line Adjustable Disinfectant/Sanitizer/Bleach Generator, and U.S. Patent Application Publication No. U.S. 2012/0171076, entitled Water Temperature as a Means of Controlling Kinetics of Onsite Generated Peracids, each filed concurrently herewith. For example, the reagents can be sequentially added to a reaction vessel, and mixed for an amount of time effective to form the desired percarboxylic acid concentration. Alternatively, the reagents can be added substantially simultaneously to a reaction vessel, and mixed for an amount of time effective to form the desired percarboxylic acid concentration. In some embodiments, the reagents are mixed for about 5 to about 30 minutes. In other embodiments, the reagents are mixed for about 10, about 15, about 20, or about 25 minutes.

In some embodiments, a mixed percarboxylic acid composition is formed by using more than one ester of a polyhydric alcohol and a C1 to C18 carboxylic acid as starting reagents and/or more than form of an ester of a polyhydric alcohol and a C1 to C18 carboxylic acid as starting reagents (e.g. mono, di, tri or mixtures thereof for ester formations). For example, in some embodiments, a mixed percarboxylic acid composition including peracetic acid and peroctanoic acid is formed. To form this composition, an ester of a polyhydric alcohol and a C2 carboxylic acid is combined with an ester of a polyhydric alcohol and a C8 carboxylic acid, a source of alkalinity, and an oxidizing agent.

When forming a mixed peracid composition, the order of addition can be varied depending on the reaction conditions. For example, in some embodiments, all of the reagents can be combined and mixed in one step. Alternatively, in some embodiments, one of the esters can be added to a reaction vessel, with an oxidizing agent, and a source of alkalinity added sequentially. This mixture can be allowed to react for an effective amount of time, prior to the second ester being added to the reaction mixture. Preparing the mixed percarboxylic acid system in a stepwise manner also allows for control of the reaction temperature. For example, by splitting the perhydrolysis reactions into two steps, the overall temperature of the reaction mixture is lower.

The order of addition and time for reaction can be varied according to the desired percarboxylic acid composition. That is, the reaction can be controlled so as to favor the reaction conditions for formation of each of the percarboxylic acids individually. For example, if it is known that one of the esters has a kinetically slower perhydrolysis reaction rate, that ester can be added to the reaction vessel first. After an amount of time sufficient to maximize the percarboxylic acid formation of the first ester, the second ester with a kinetically faster perhydrolysis reaction rate can be added to the reaction vessel.

The order of mixing and addition of reagents can be used to control the production of the percarboxylic acid composition, namely to ensure a consistent output of chemistry without any fouling (e.g. precipitation) of the reagents. In one aspect of the invention, the source of alkalinity (e.g. sodium hydroxide or caustic soda) is combined with water (e.g. diluted) prior to the addition of the ester source.

The concentration of reagents, in addition to mixing order, can further be used to control the production of the percarboxylic acid composition. In a preferred embodiment, the concentration of the source of alkalinity is diluted to produce a consistent output of chemistry without any fouling (e.g. precipitation) of the reagents. In one aspect the concentrated alkaline solution (e.g. NaOH) is diluted with a water source before the ester component is combined with the reagents. Although not intending to be limited according to any theory of the invention and/or mechanism of action, the invention demonstrates superior chemistry generation when a system delivers a source of alkalinity (e.g. NaOH solution) that is no more than about 50%, preferably no more than about 40% on an actives basis before combining with the ester reagent to initiate the peracid production reaction.

In some aspects, the present disclosure provides methods for forming an antimicrobial composition. The methods include providing a mixed peroxycarboxylic acid forming composition. The mixed peroxycarboxylic acid forming composition includes: a first ester of a polyhydric alcohol and a C1 to C18 carboxylic acid, for example a C1 to C4 carboxylic acid; a second ester of a polyhydric alcohol and a C1 to C18 carboxylic acid, for example a C8 to C11 carboxylic acid; a source of alkalinity; and an oxidizing agent. After allowing the reaction mixture to react for a sufficient amount of time, a mixed percarboxylic acid composition is formed. The mixed peroxycarboxylic acid composition is diluted with an acidic aqueous solution. In some embodiments, the mixed peroxycarboxylic acid composition is diluted with an amount of an acidic aqueous solution effective to provide the diluted disinfecting composition with a pH of about 1.0 to about 8.0. In other aspects, the present disclosure provides methods for forming a disinfecting composition including a single percarboxylic acid. The methods include providing a peroxycarboxylic acid forming composition. The composition includes: an ester of a polyhydric alcohol and a C1 to C18 carboxylic acid; a source of alkalinity; and an oxidizing agent, wherein said composition has a pH greater than 12. The peroxycarboxylic acid forming composition is then diluted with an acidic aqueous solution. In some embodiments, the diluted acidic peroxycarboxylic acid composition has a pH of about 1.0 to about 8.0.

Any acidic solution can be used to dilute the peroxycarboxylic acid compositions. In an embodiment, the acidulant includes an inorganic acid. Suitable inorganic acids include, but are not limited to, sulfuric acid, sodium bisulfate, phosphoric acid, nitric acid, hydrochloric acid. In some embodiments, the acidulant includes an organic acid. Suitable organic acids include, but are not limited to, methane sulfonic acid, ethane sulfonic acid, propane sulfonic acid, butane sulfonic acid, xylene sulfonic acid, cumene sulfonic acid, benzene sulfonic acid, formic acid, acetic acid, mono, di, or tri-halocarboyxlic acids, picolinic acid, dipicolinic acid, and mixtures thereof. In some embodiments, the compositions of the present invention are free or substantially free of a phosphorous based acid.

In an aspect the acid or acidic solution acidifies the peroxycarboxylic acid forming composition to the peroxycarboxylic acid composition. In a further aspect, the use of an acid or acidic solution dilutes the peroxycarboxylic acid compositions. Methods employing the acidification of the peroxycarboxylic acid forming composition further stabilize the composition. However, as one skilled in the art will appreciate, some reaction intermediates of the peroxycarboxylic acid forming composition are stable for sufficient periods of time and do not need to be acidified immediately. For example, some reaction intermediates are stable for at least 24 hours and can be utilized in an on-site application without the acidification step for further dilution and/or stabilization. Other peroxycarboxylic acid forming compositions are less stable and the perhydrolysis reaction requires quenching with the acid or acidic aqueous solution to lower the pH and stabilize more promptly.

In another aspect of the invention, the peroxycarboxylic acid forming compositions are acidified within a cleaning application or within a use system (i.e., post generator within a customer's process). One primary differentiator between industrial or institutional laundry and consumer laundry is that typically there are multiple products that are automatically dosed. For alkaline laundry, as is common in industrial and institutional accounts, an acid may optionally be dosed at the end of the wash to neutralize and remaining alkalinity. This acid could also be used for post generator acidification of the alkaline peracids of this invention, within the washing machine itself.

Methods for Making Using Concentrated Premix Formulations

In some aspects, the present disclosure provides methods for making the peroxycarboxylic acid compositions disclosed herein using concentrated premix formulations. Without limiting the scope of the invention and the methods for making the compositions disclosed herein, the same methods of making can be employed utilizing various concentrated premix formulations to combine the at least one ester of a polyhydric alcohol and a C1 to C18 carboxylic acid, a source of alkalinity and an oxidizing agent. The use of concentrated premix formulations minimizes the number of composition reagents according to the invention to simplify the methods even further.

The use of various concentrated premix formulations according to the invention does not alter the remaining method steps-only the input of reagents to a system using the methods of the invention. Upon combining a particular concentrated premix formulation with the remaining reagents the reaction mixture allows for the perhydrolysis of the ester to form the corresponding C1 to C18 peroxycarboxylic acid. Without wishing to be bound by any particular theory it is thought that the oxidizing agent present perhydrolyzes the ester bonds, thereby forming the corresponding percarboxylic acids.

According to an exemplary method of making the peroxycarboxylic acid compositions, a concentrated premix formulation comprising the ester(s) and oxidizing agent are mixed with the alkalinity source to form concentrated peracid chemistry. As disclosed herein, the alkalinity source may be a diluted alkaline solution (e.g. NaOH) obtained by diluting the alkaline source with a water source before the concentrated premix comprising the ester component is combined with the dilute alkaline source.

The generated concentrated peracid chemistry according to the invention, regardless of whether generated using individual reagent sources and/or concentrated premix formulations, remains stable from a few hours to a few days. The on-site generated compositions according to the invention obviate the need of various stabilizing agents as the chemistry is used on-site and not shipped and/or maintained in storage for any significant period of time.

The generated concentrated peracid chemistry may be diluted according to a particular use. For example, in an embodiment, the concentrated peracid chemistry is added to a post dilution tank or reservoir where water may be used to dilute the concentrated chemistry into a dispersion of the alkaline solution in water. This step may be referred to as generating an intermediate dilution. Without being limited to a particular theory of the invention, the dilution of the concentrated chemistry into an intermediate dilution in an alkaline solution maintains the phase stability of the peracid chemistry. In one aspect the solution may be diluted to about 100 ppm to about 10,000 ppm solution, preferably to about 1,000 ppm to about 4,000 ppm, and more preferably to about 1,000 ppm solution (e.g. about 0.1% active peracid). Thereafter the acidification of the diluted peracid chemistry may take place without any fouling of the chemistry. Thereafter the diluted peracid chemistry may be sourced to various use applications at very dilute amounts as a result of the on-site generation. For example, diluted peracid chemistry may be added into a use solution with concentrations less than about 10 ppm, less than about 50 ppm or less than about 100 ppm, without the wasteful shipment of such diluted chemistries.

As one skilled in the art will ascertain the method of making the peracid compositions, in particular the various dilutions of the concentrated peracid chemistries and/or acidification steps, may not be required depending upon the particular use applications of the chemistry. For example, a non-limiting example includes the use of concentrated peracid chemistry for certain textile and/or bleaching applications. In such an embodiment, the concentrated peracid chemistry does not require the dilution in an alkaline solution to an intermediate solution having an active chemistry concentration of from about 100 ppm to about 10,000 ppm.

Rather the concentrated alkaline chemistry could be immediately sourced to an application of use (e.g. textile cleaning and/or bleaching).

Methods for Using Compositions for Bleaching and Antimicrobial Agents

The related filings disclosed herein provide for compositions, methods of making the compositions and/or methods of using or employing the compositions of the invention along with disclosing various applications for use. According to the invention presented herein, various laundry applications, including textile care and on-premise laundry applications are particularly well suited for the application of the present invention.

In some aspects the compositions can be used in various industrial processes, including for example, treating waste water where both its antimicrobial function and its oxidant properties can be utilized. In addition to the antimicrobial uses according to the invention, there are often concerns with waste water being rich in malodorous compounds of reduced sulfur, nitrogen or phosphorous. A strong oxidant such as that generated according to the present invention converts these compounds efficiently to their odor free derivatives e.g. the sulfates, phosphates and amine oxides. These same properties are very useful in the pulp and paper industry where the property of bleaching is also of great utility.

In another aspect, the compositions can be used in a variety of domestic or industrial applications, e.g., to reduce microbial or viral populations on a surface or object or in a body or stream of water, as disclosed in the related applications and incorporated herein by reference. For example, the compounds can be applied in a variety of areas including a variety of hard or soft surfaces having smooth, irregular or porous topography. Suitable hard surfaces include, for example, architectural surfaces (e.g., floors, walls, windows, sinks, tables, counters and signs); eating utensils; hard-surface medical or surgical instruments and devices; and hard-surface packaging. Such hard surfaces can be made from a variety of materials including, for example, ceramic, metal, glass, wood or hard plastic. Suitable soft surfaces include, for example paper; filter media; hospital and surgical linens and garments; soft-surface medical or surgical instruments and devices; and soft-surface packaging. Such soft surfaces can be made from a variety of materials including, for example, paper, fiber, woven or nonwoven fabric, soft plastics and elastomers. The compounds of the invention can also be applied to soft surfaces such as food and skin (e.g., a hand). The present compounds can be employed as a foaming or nonfoaming environmental sanitizer or disinfectant.

In some aspects, the present disclosure includes methods of using the peroxycarboxylic acid compositions for antimicrobial and/or bleaching activity for textile and/or laundry applications. In one aspect, the methods include using a mixed peroxycarboxylic acid compositions wherein more than one peroxycarboxylic acids are formed on-sited according to the methods of generating the chemistry for synergy in efficacy compared to the use of a single peroxycarboxylic acid compositions. In a further aspect, the methods include using a mixed peroxycarboxylic acid compositions in combination with a surfactant for additional synergy in efficacy beyond that provided by use with the peroxycarboxylic acid compositions according to the invention.

In some aspects, the present disclosure includes methods of using the peroxycarboxylic acid compositions disclosed herein. In some aspects, the methods of using the compositions employ a chemistry having a pH of from about 0 to about 5 for various antimicrobial applications. In other aspects, the methods of using the compositions employ a chemistry having a pH of from about 5 to about 10 for various antimicrobial applications. In still further aspects, the methods of using the compositions employ a chemistry having a pH of from about 5 to about 14 for various bleaching applications.

In some embodiments, these methods employ the antimicrobial and/or bleaching activity of the compositions for textile and/or laundry applications. For example, the invention includes a method for reducing a microbial population, a method for reducing the population of spores, a method for reducing an odor, and/or a method for bleaching. These methods preferably operate on an article, surface, in a body or stream of water or a gas, or the like, by contacting the article, surface, body, or stream with the compositions.

The compositions of the present invention can also be used for laundry or textile applications. The compositions can be employed by rinsing laundry or textile surfaces with the use solution, keeping the surfaces wet for a sufficient time to wash, de-stain, sanitize, bleach and/or rinse the surface.

In embodiments for laundry treatments, namely a method for treating laundry, various items or articles may be cleaned in a laundry application, such as a washing machine. Laundry suitable for cleaning, bleaching and/or disinfecting according to the invention includes, for example, any item or article made from or including textile materials, woven fabrics, non-woven fabrics, and knitted fabrics. The textile materials can include natural or synthetic fibers such as silk fibers, linen fibers, cotton fibers, polyester fibers, polyamide fibers such as nylon, acrylic fibers, acetate fibers, and blends thereof including cotton and polyester blends. The fibers can be treated or untreated. The term "linen" is often used to describe certain types of laundry items including bed sheets, pillow cases, towels, table linen, table cloth, bar mops and uniforms. The invention additionally includes the cleaning, bleaching and/or disinfecting of non-laundry articles and surfaces including hard surfaces such as dishes, glasses, and other ware.

The methods may also include contacting the article, surface, in a body or stream of water or a gas, or the like, in combination with a surfactant for synergistic efficacy. Contacting can include any of numerous methods for applying the compositions, such as spraying the compositions, immersing the article in the compositions, foam or gel treating the article with the compositions, or the like or a combination thereof.

In some aspects, the compositions are present at an amount effective for killing one or more of various pathogenic microorganisms, including bacteria, including, but not limited to, *Salmonella, Staphylococcus, Campylobacter, Pseudomonas, Listeria, Streptococci, Legionella, Escherichia coli, tuberculosis*, phages, mycobacteria, yeast, mold, fungi, spores, viruses, or the like. The compositions of the present invention have activity against a wide variety of microorganisms such as Gram positive (for example, *Listeria monocytogenes* or *Staphylococcus aureus*) and Gram negative (for example, *Escherichia coli* or *Pseudomonas aeruginosa*) bacteria, yeast, molds, bacterial spores, viruses, etc. In addition, the compositions, as described above, have activity against a wide variety of human pathogens.

The compositions can be used for a variety of domestic or industrial applications, e.g., to reduce microbial or viral populations on a surface or object or in a body or stream of water. The compositions can be applied in a variety of areas and surfaces, including a variety of hard or soft surfaces having smooth, irregular or porous topography. Such hard and soft surfaces can be made from a variety of materials as one skilled in the art will ascertain. Examples of suitable soft surfaces include, textiles, including for example, hospital and surgical linens and garments. Such soft surfaces can be made from a variety of materials including, for example, paper, fiber, woven or nonwoven fabric, soft plastics and elastomers.

The compositions of the invention can be included in products such as sterilants, sanitizers, disinfectants, preservatives, deodorizers, antiseptics, fungicides, germicides, sporicides, virucides, detergents, bleaches, hard surface cleaners, hand soaps, waterless hand sanitizers, and pre- or post-surgical scrubs.

The peroxycarboxylic acid laundry treatment composition can provide for bleaching and antimicrobial treatment and can be referred to as the bleaching and antimicrobial composition or more simply as the treatment composition. The composition can be provided in the form of a concentrated chemistry that is diluted with water to provide a use solution. The use solution can be used for washing articles such as laundry.

A concentrate or use concentration of the compositions can be applied to or brought into contact with a surface and/or an object by any conventional method or apparatus for applying an antimicrobial or cleaning compound to an object. For example, the object can be wiped with, sprayed with, foamed on, and/or immersed in the compositions, or a use solution made from the compositions. The compositions can be sprayed, foamed, or wiped onto a surface; the compositions can be caused to flow over the surface, or the surface can be dipped into the compositions. Contacting can be manual or by machine.

The method for treating laundry according to the invention can be provided as part of an overall method for cleaning laundry according to the invention. That is, as part of a laundry cleaning operation, the laundry can be treated with a bleaching and antimicrobial composition to provide bleaching and antimicrobial properties. In addition, the laundry can be treated with a bleaching and antimicrobial composition in combination with a surfactant source to provide synergistic bleaching and antimicrobial properties. Any suitable surfactant for use in laundry applications may be used according to the invention. Notably, the surfactant is used after the generation of the peroxycarboxylic acid laundry treatment composition according to the invention. Therefore, one skilled in the art will ascertain that such surfactant is not a component added the system for establishing and/or maintaining the stability of the peroxycarboxylic acid laundry treatment composition. As has been previously described herein, the peroxycarboxylic acid composition do not require and/or employ the use of stabilizing agents, including surfactants, for establishing and/or maintaining phase stability of the composition.

Suitable surfactants for use in detergents to be combined with the peroxycarboxylic acid laundry treatment compositions according to the invention include any suitable surfactants for use in laundry applications, including, but not limited to, nonionic surfactants, anionic surfactants, cationic surfactants and zwitterionic surfactants.

Suitable nonionic surfactants for use with the compositions of the present invention include alkoxylated surfactants. Suitable alkoxylated surfactants include ethylene oxide, propylene oxide, butylenes oxide (EO/PO/BO) copolymers, capped EO/PO/BO copolymers, alcohol alkoxylates, capped alcohol alkoxylates, mixtures thereof, or the like. Especially suitable nonionic surfactants for use with the present invention include low alkoylated surfactants, including those with one or two EO/PO/BO units, such as Lutensol TO 2, which contains a branched C13 hydrophobe and two EO units. Suitable alkoxylated surfactants for use as solvents include EO/PO block copolymers, such as the Pluronic and reverse Pluronic surfactants; alcohol alkoxylates, such as Dehypon LS-54 (R-(EO)$_5$(PO)$_4$) and Dehypon LS-36 (R-(EO)$_3$(PO)$_6$); and capped alcohol alkoxylates, such as Plurafac LF221 and Tegoten EC11; mixtures thereof, or the like.

Semi-Polar Nonionic Surfactants

The semi-polar type of nonionic surface active agents are another class of nonionic surfactant useful in compositions of the present invention. Semi-polar nonionic surfactants include the amine oxides, phosphine oxides, sulfoxides and their alkoxylated derivatives.

Amine oxides are tertiary amine oxides corresponding to the general formula:

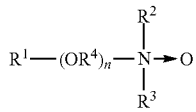

wherein the arrow is a conventional representation of a semi-polar bond; and, $R^1$, $R^2$, and $R^3$ may be aliphatic, aromatic, heterocyclic, alicyclic, or combinations thereof. Generally, for amine oxides of detergent interest, $R^1$ is an alkyl radical of from about 8 to about 24 carbon atoms; $R^2$ and $R^3$ are alkyl or hydroxyalkyl of 1-3 carbon atoms or a mixture thereof; $R^2$ and $R^3$ can be attached to each other, e.g. through an oxygen or nitrogen atom, to form a ring structure; $R^4$ is an alkylene or a hydroxyalkylene group containing 2 to 3 carbon atoms; and n ranges from 0 to about 20. An amine oxide can be generated from the corresponding amine and an oxidizing agent, such as hydrogen peroxide.

Useful water soluble amine oxide surfactants are selected from the octyl, decyl, dodecyl, isododecyl, coconut, or tallow alkyl di-(lower alkyl)amine oxides, specific examples of which are octyldimethylamine oxide, nonyldimethylamine oxide, decyldimethylamine oxide, undecyldimethylamine oxide, dodecyldimethylamine oxide, iso-dodecyldimethyl amine oxide, tridecyldimethylamine oxide, tetradecyldimethylamine oxide, pentadecyldimethylamine oxide, hexadecyldimethylamine oxide, heptadecyldimethylamine oxide, octadecyldimethylaine oxide, dodecyldipropylamine oxide, tetradecyldipropylamine oxide, hexadecyldipropylamine oxide, tetradecyldibutylamine oxide, octadecyldibutylamine oxide, bis(2-hydroxyethyl)dodecylamine oxide, bis(2-hydroxyethyl)-3-dodecoxy-1-hydroxypropylamine oxide, dimethyl-(2-hydroxydodecyl)amine oxide, 3,6,9-trioctadecyldimethylamine oxide and 3-dodecoxy-2-hydroxypropyldi-(2-hydroxyethyl)amine oxide.

Anionic Surfactants

Anionic sulfate surfactants suitable for use in the present compositions include alkyl ether sulfates, alkyl sulfates, the linear and branched primary and secondary alkyl sulfates, alkyl ethoxysulfates, fatty oleyl glycerol sulfates, alkyl phenol ethylene oxide ether sulfates, the $C_5$-$C_{17}$ acyl-N—($C_1$-$C_4$ alkyl) and —N—($C_1$-$C_2$ hydroxyalkyl) glucamine sulfates, and sulfates of alkylpolysaccharides such as the sulfates of alkylpolyglucoside, and the like. Also included are the alkyl sulfates, alkyl poly(ethyleneoxy) ether sulfates and aromatic poly(ethyleneoxy) sulfates such as the sulfates or condensation products of ethylene oxide and nonyl phenol (usually having 1 to 6 oxyethylene groups per molecule). Anionic sulfonate surfactants suitable for use in the present compositions also include alkyl sulfonates, the linear and branched primary and secondary alkyl sulfonates, and the aromatic sulfonates with or without substituents.

Anionic carboxylate surfactants suitable for use in the present compositions include carboxylic acids (and salts), such as alkanoic acids (and alkanoates), ester carboxylic acids (e.g. alkyl succinates), ether carboxylic acids, and the like. Such carboxylates include alkyl ethoxy carboxylates, alkyl aryl ethoxy carboxylates, alkyl polyethoxy polycarboxylate surfactants and soaps (e.g. alkyl carboxyls). Secondary carboxylates useful in the present compositions include those which contain a carboxyl unit connected to a secondary carbon. The secondary carbon can be in a ring structure, e.g. as in p-octyl benzoic acid, or as in alkyl-substituted cyclohexyl carboxylates. The secondary carboxylate surfactants typically contain no ether linkages, no ester linkages and no hydroxyl groups. Further, they typically lack nitrogen atoms in the head-group (amphiphilic portion). Suitable secondary soap surfactants typically contain 11-13 total carbon atoms, although more carbons atoms (e.g., up to 16) can be present. Suitable carboxylates also include acylamino acids (and salts), such as acylgluamates, acyl peptides, sarcosinates (e.g. N-acyl sarcosinates), taurates (e.g. N-acyl taurates and fatty acid amides of methyl tauride), and the like.

Suitable anionic surfactants include alkyl or alkylaryl ethoxy carboxylates of the following formula:

$$R-O-(CH_2CH_2O)_n(CH_2)_m-CO_2X \quad (3)$$

in which R is a $C_8$ to $C_{22}$ alkyl group or

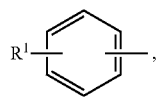

in which $R^1$ is a $C_4$-$C_{16}$ alkyl group; n is an integer of 1-20; m is an integer of 1-3; and X is a counter ion, such as hydrogen, sodium, potassium, lithium, ammonium, or an amine salt such as monoethanolamine, diethanolamine or triethanolamine. In some embodiments, n is an integer of 4 to 10 and m is 1. In some embodiments, R is a $C_8$-$C_{16}$ alkyl group. In some embodiments, R is a $C_{12}$-$C_{14}$ alkyl group, n is 4, and m is 1.

In other embodiments, R is

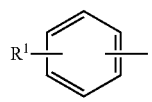

and $R^1$ is a $C_6$-$C_{12}$ alkyl group. In still yet other embodiments, $R^1$ is a $C_9$ alkyl group, n is 10 and m is 1.

Such alkyl and alkylaryl ethoxy carboxylates are commercially available. These ethoxy carboxylates are typically available as the acid forms, which can be readily converted to the anionic or salt form. Commercially available carboxylates include, Neodox 23-4, a $C_{12-13}$ alkyl polyethoxy (4) carboxylic acid (Shell Chemical), and Emcol CNP-110, a $C_9$ alkylaryl polyethoxy (10) carboxylic acid (Witco Chemical). Carboxylates are also available from Clariant, e.g. the product Sandopan® DTC, a $C_{13}$ alkyl polyethoxy (7) carboxylic acid.

Amphoteric Surfactants

Amphoteric, or ampholytic, surfactants contain both a basic and an acidic hydrophilic group and an organic hydrophobic group. These ionic entities may be any of anionic or cationic groups described herein for other types of surfactants. A basic nitrogen and an acidic carboxylate group are the typical functional groups employed as the basic and acidic hydrophilic groups. In a few surfactants, sulfonate, sulfate, phosphonate or phosphate provide the negative charge.

Amphoteric surfactants can be broadly described as derivatives of aliphatic secondary and tertiary amines, in which the aliphatic radical may be straight chain or branched and wherein one of the aliphatic substituents contains from about 8 to 18 carbon atoms and one contains an anionic water solubilizing group, e.g., carboxy, sulfo, sulfato, phosphato, or phosphono. Amphoteric surfactants are subdivided into two major classes known to those of skill in the art and described in "Surfactant Encyclopedia" Cosmetics & Toiletries, Vol. 104 (2) 69-71 (1989). The first class includes acyl/dialkyl ethylenediamine derivatives (e.g. 2-alkyl hydroxyethyl imidazoline derivatives) and their salts. The second class includes N-alkylamino acids and their salts. Some amphoteric surfactants can be envisioned as fitting into both classes.

Amphoteric surfactants can be synthesized by methods known to those of skill in the art. For example, 2-alkyl hydroxyethyl imidazoline is synthesized by condensation and ring closure of a long chain carboxylic acid (or a derivative) with dialkyl ethylenediamine. Commercial amphoteric surfactants are derivatized by subsequent hydrolysis and ring-opening of the imidazoline ring by alkylation—for example with chloroacetic acid or ethyl acetate. During alkylation, one or two carboxy-alkyl groups react to form a tertiary amine and an ether linkage with differing alkylating agents yielding different tertiary amines.

Long chain imidazole derivatives having application in the present invention generally have the general formula:

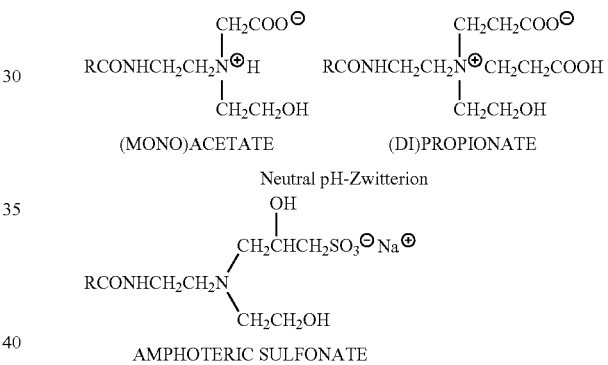

wherein R is an acyclic hydrophobic group containing from about 8 to 18 carbon atoms and M is a cation to neutralize the charge of the anion, generally sodium. Commercially prominent imidazoline-derived amphoterics that can be employed in the present compositions include for example: Cocoamphopropionate, Cocoamphocarboxy-propionate, Cocoamphoglycinate, Cocoamphocarboxy-glycinate, Cocoamphopropyl-sulfonate, and Cocoamphocarboxy-propionic acid. Amphocarboxylic acids can be produced from fatty imidazolines in which the dicarboxylic acid functionality of the amphodicarboxylic acid is diacetic acid and/or dipropionic acid.

The carboxymethylated compounds (glycinates) described herein above frequently are called betaines. Betaines are a special class of amphoteric discussed herein below in the section entitled, Zwitterion Surfactants.

Long chain N-alkylamino acids are readily prepared by reaction $RNH_2$, in which $R=C_8$-$C_{18}$ straight or branched chain alkyl, fatty amines with halogenated carboxylic acids. Alkylation of the primary amino groups of an amino acid leads to secondary and tertiary amines. Alkyl substituents may have additional amino groups that provide more than one reactive nitrogen center. Most commercial N-alkylamine acids are alkyl derivatives of beta-alanine or beta-N(2-carboxyethyl)alanine Examples of commercial N-alkylamino acid ampholytes having application in this invention include alkyl beta-amino dipropionates, $RN(C_2H_4COOM)_2$ and $RNHC_2H_4COOM$. In an embodiment, R can be an acyclic hydrophobic group containing from about 8 to about 18 carbon atoms, and M is a cation to neutralize the charge of the anion.

Suitable amphoteric surfactants include those derived from coconut products such as coconut oil or coconut fatty acid. Additional suitable coconut derived surfactants include as part of their structure an ethylenediamine moiety, an alkanolamide moiety, an amino acid moiety, e.g., glycine, or a combination thereof; and an aliphatic substituent of from about 8 to 18 (e.g., 12) carbon atoms. Such a surfactant can also be considered an alkyl amphodicarboxylic acid. These amphoteric surfactants can include chemical structures represented as: $C_{12}$-alkyl-C(O)—NH—$CH_2$—$CH_2$—$N^+(CH_2$—$CH_2$—$CO_2Na)_2$—$CH_2$—$CH_2$—OH or $C_{12}$-alkyl-C(O)—N(H)—$CH_2$—$CH_2$-$N^+(CH_2$—$CO_2Na)_2$—$CH_2$—$CH_2$—OH. Disodium cocoampho dipropionate is one suitable amphoteric surfactant and is commercially available under the tradename Miranol™ FBS from Rhodia Inc., Cranbury, N.J. Another suitable coconut derived amphoteric surfactant with the chemical name disodium cocoampho diacetate is sold under the tradename Mirataine™ JCHA, also from Rhodia Inc., Cranbury, N.J.

A typical listing of amphoteric classes, and species of these surfactants, is given in U.S. Pat. No. 3,929,678 issued to Laughlin and Heuring on Dec. 30, 1975. Further examples are given in "Surface Active Agents and Detergents" (Vol. I and II by Schwartz, Perry and Berch).

Zwitterionic Surfactants

Zwitterionic surfactants can be thought of as a subset of the amphoteric surfactants and can include an anionic charge. Zwitterionic surfactants can be broadly described as derivatives of secondary and tertiary amines, derivatives of heterocyclic secondary and tertiary amines, or derivatives of quaternary ammonium, quaternary phosphonium or tertiary sulfonium compounds. Typically, a zwitterionic surfactant includes a positive charged quaternary ammonium or, in some cases, a sulfonium or phosphonium ion; a negative charged carboxyl group; and an alkyl group. Zwitterionics generally contain cationic and anionic groups which ionize to a nearly equal degree in the isoelectric region of the molecule and which can develop strong "inner-salt" attraction between positive-negative charge centers. Examples of such zwitterionic synthetic surfactants include derivatives of aliphatic quaternary ammonium, phosphonium, and sulfonium compounds, in which the aliphatic radicals can be straight chain or branched, and wherein one of the aliphatic substituents contains from 8 to 18 carbon atoms and one contains an anionic water solubilizing group, e.g., carboxy, sulfonate, sulfate, phosphate, or phosphonate. Betaine and sultaine surfactants are exemplary zwitterionic surfactants for use herein.

A general formula for these compounds is:

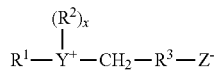

wherein $R^1$ contains an alkyl, alkenyl, or hydroxyalkyl radical of from 8 to 18 carbon atoms having from 0 to 10 ethylene oxide moieties and from 0 to 1 glyceryl moiety; Y is selected from the group consisting of nitrogen, phosphorus, and sulfur atoms; $R^2$ is an alkyl or monohydroxy alkyl group containing 1 to 3 carbon atoms; x is 1 when Y is a sulfur atom and 2 when Y is a nitrogen or phosphorus atom, $R^3$ is an alkylene or hydroxy alkylene or hydroxy alkylene of from 1 to 4 carbon atoms and Z is a radical selected from the group consisting of carboxylate, sulfonate, sulfate, phosphonate, and phosphate groups.

Examples of zwitterionic surfactants having the structures listed above include: 4-[N,N-di(2-hydroxyethyl)-N-octadecylammonio]-butane-1-carboxylate; 5-[S-3-hydroxypropyl-S-hexadecylsulfonio]-3-hydroxypentane-1-sulfate; 3-[P,P-diethyl-P-3,6,9-trioxatetracosanephosphonio]-2-hydroxypropane-1-phosphate; 3-[N,N-dipropyl-N-3-dodecoxy-2-hydroxypropyl-ammonio]-propane-1-phosphonate; 3-(N,N-dimethyl-N-hexadecylammonio)-propane-1-sulfonate; 3-(N,N-dimethyl-N-hexadecylammonio)-2-hydroxy-propane-1-sulfonate; 4-[N,N-di(2(2-hydroxyethyl)-N(2-hydroxydodecyl)ammonio]-butane-1-carboxylate; 3-[S-ethyl-S-(3-dodecoxy-2-hydroxypropyl)sulfonio]-propane-1-phosphate; 3-[P,P-dimethyl-P-dodecylphosphonio]-propane-1-phosphonate; and S [N,N-di(3-hydroxypropyl)-N-hexadecylammonio]-2-hydroxy-pentane-1-sulfate. The alkyl groups contained in said detergent surfactants can be straight or branched and saturated or unsaturated.

The zwitterionic surfactant suitable for use in the present compositions includes a betaine of the general structure:

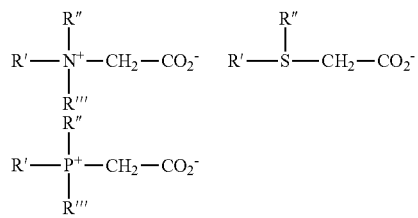

These surfactant betaines typically do not exhibit strong cationic or anionic characters at pH extremes nor do they show reduced water solubility in their isoelectric range. Unlike "external" quaternary ammonium salts, betaines are compatible with anionics. Examples of suitable betaines include coconut acylamidopropyldimethyl betaine; hexadecyl dimethyl betaine; $C_{12-14}$ acylamidopropylbetaine; $C_{8-14}$ acylamidohexyldiethyl betaine; 4-$C_{14-16}$ acylmethylamidodiethylammonio-1-carboxybutane; $C_{16-18}$ acylamidodimethylbetaine; $C_{12-16}$ acylamidopentanediethylbetaine; and $C_{12-16}$ acylmethylamidodimethylbetaine.

Sultaines useful in the present invention include those compounds having the formula $(R(R^1)_2N^+R^2SO^{3-}$, in which R is a $C_6$-$C_{18}$ hydrocarbyl group, each $R^1$ is typically independently $C_1$-$C_3$ alkyl, e.g. methyl, and $R^2$ is a $C_1$-$C_6$ hydrocarbyl group, e.g. a $C_1$-$C_3$ alkylene or hydroxyalkylene group.

A typical listing of zwitterionic classes, and species of these surfactants, is given in U.S. Pat. No. 3,929,678 issued to Laughlin and Heuring on Dec. 30, 1975. Further examples are given in "Surface Active Agents and Detergents" (Vol. I and II by Schwartz, Perry and Berch).

In an embodiment, the compositions of the present invention include a betaine. For example, the compositions can include cocoamido propyl betaine.

The use of surfactants as detergents according to the invention is distinct from the combined use of bleach activators (to generate peroxycarboxylic acids in situ within a washing wheel or machine) and detergents described in various prior art applications. See for example the disclosure of in situ production disclosed in U.S. Pat. Nos. 4,367,156, 4,681,593 and 5,019,292, and WO1994018299, all references incorporated herein by reference. In particular, as set forth in the methods of the present invention, the peroxycarboxylic acid compositions are not generated in-situ (e.g. within a washing wheel or machine), rather the peroxycarboxylic acid compositions are generated ex situ from the point of use. The methods of making the peroxycarboxylic acid compositions demonstrate that the generation of the peroxycarboxylic acids requires conditions not found within the washing point of use. For example, the methods of making the peroxycarboxylic acid compositions require a reaction mixture that is not at equilibrium and is reacted for a particular amount of time at a pH of above at least 12. Thereafter generation of the peroxycarboxylic acid compositions may optionally be combined with a surfactant and/or detergent down the line from the generation of the peroxycarboxylic acids. Accordingly, an already generated peroxycarboxylic acid composition (at a user preferred dilution and percent actives) is provided to a point of use, namely a laundry application.

The methods of use and generation according to the invention are distinct from the in-situ generation of peroxycarboxylic acids in existing commercial products. Beneficially, generating the peroxycarboxylic acid compositions according to the methods of the present invention reduce the need for reagents compared to an equilibrium peracid system (e.g. reducing waste) as well as obtain an increased amount of peroxycarboxylic acids generated compared to in situ generation in the wash bath via a conventional bleach activator. According to an embodiment the methods of the invention generate peracid yields from about 0.25% to about 20%. In some aspects, the methods of the invention generate peracid yields of at least about 2%, at least about 3%, preferably at least about 4%, more preferably at least about 5%, and still most preferably at least about 6% peracid yield from the reaction mixtures (reagents). In addition to the increased generation of peracid yield according to the invention, the rates of generation are further preferential, obtaining the desired peracid yield within a matter of minutes, preferably within about 5 minutes.

According to the invention, the bleaching and/or antimicrobial properties can be characterized as sanitizing when there is a substantial reduction of bacteria, fungi, spores, and other microorganisms or microorganism generating materials on a surface being treated to provide a sanitized surface. A substantial reduction refers to a reduction of at least three orders of magnitude. Preferably, the reduction can be at least five orders of magnitude. A cleaning process according to the invention can include all three of the removal of soil, the removal of staining or the appearance of staining, and the reduction of a population of microbes.

The method for treating laundry according to the invention can be provided in a commercial and/or industrial laundry washing facility and can be provided in a residential and/or home laundry washing machine. Exemplary commercial and/or industrial laundry washing facilities include those cleaning textiles for the rental, health care, and hospitality industries. In addition, the method for treating laundry can occur as part of an operation that includes additional steps, such as, washing, rinsing, finishing, and extracting. In addition, it should be understood that the step of treating laundry can include, as part of the step, additional activities such as, for example, washing and finishing.

It is expected that many commercial and industrial laundry washing machines are capable of handling the method for treating laundry according to the invention. Many commercial and industrial laundry washing machines are computer programmable, and computer programs can be provided to operate the machines according to the invention. In addition, it is expected that machines can be made available to treat laundry according to the invention, and that these machines can be used in both industrial and commercial applications and in home and residential applications. In addition, the treatment composition can be formulated so that it can be used in commercial and industrial laundry washing machines and residential laundry washing machines that are in common use, that are not computer programmable, and without modification. That is, it is expected that conventional laundry washing machines can be used to treat laundry according to the invention.

In an embodiment of the invention, the treated objects under a laundry washing step in the presence of both a detergent use solution and the peroxycarboxylic acid compositions. In one aspect, a portion of a detergent use solution can be drained from the laundry prior to the step of adding the peroxycarboxylic acid compositions according to the invention. Alternatively, at least a portion of the detergent use solution can be drained from the laundry and the laundry can be rinsed to further remove the detergent use solution from the laundry prior to the step of treating the laundry with the peroxycarboxylic acid compositions. Various techniques for washing laundry with a detergent use solution can be utilized according to the invention for cleaning laundry prior and/or concomitantly with the step of treating with the peroxycarboxylic acid compositions according to the invention.

The detergent use solution for use in combination with the peroxycarboxylic acid compositions for synergistic efficacy can be an alkaline or an acid detergent use solution. Techniques for acid cleaning are described in German Publication No. DE 101 50 403, the entire disclosure of which is incorporated herein by reference. Additional techniques for acid cleaning are disclosed in U.S. application Ser. No. 10/739,922, the entire disclosure of which is incorporated herein by reference. Various techniques for cleaning that include alkaline cleaning are described in United States Patent Application Publication No. 20030162682, and U.S. Pat. No. 6,194,371, the entire disclosures of which are incorporated herein by reference. Additional techniques for cleaning laundry are described in U.S. application Ser. No. 10/600,091, the entire disclosure of which is incorporated herein by reference.

In some embodiments, it is expected that an alkaline wash refers to a wash that takes place at a pH at between about 7 and about 13, and can include a pH of between about 8 and about 12. In general, it is understood that an acid wash refers to a wash having a pH of between about 1 and about 6, and can refer to a wash having a pH in the range of about 2 to about 4.

In some embodiments, the pH of the peroxycarboxylic acid compositions can be adjusted by the introduction of a pH adjusting agent that can be an acid or a base. In some embodiments, the methods may include the use of an acidifying agent to decrease the pH of the peroxycarboxylic acid compositions. As disclosed according to embodiments of making the peroxycarboxylic acid compositions of the invention, an acid or acidic solution can be used to acidify the peroxycarboxylic acid forming composition to the peroxycarboxylic acid composition. In a further aspect, the use of an acid or acidic solution can be used to dilute the concentrated peroxycarboxylic acid compositions. In an embodiment, the acidulant includes an inorganic acid. Suitable inorganic acids include, but are not limited to, sulfuric acid, sodium bisulfate, phosphoric acid, nitric acid, hydrochloric acid. In some embodiments, the acidulant includes an organic acid. Suitable organic acids include, but are not limited to, methane sulfonic acid, ethane sulfonic acid, propane sulfonic acid, butane sulfonic acid, xylene sulfonic acid, cumene sulfonic acid, benzene sulfonic acid, formic acid, acetic acid, mono, di, or tri-halocarboyxlic acids, picolinic acid, dipicolinic acid, and mixtures thereof. In some embodiments, the compositions of the present invention are free or substantially free of a phosphorous based acid.

In an alternative embodiment a pH adjusting agent may be added to the washing application and/or at a point of use (as opposed to the dilution of the peroxycarboxylic acid compositions) to lower the pH. Exemplary acidifying agents include inorganic acids, organic acids, and mixtures of inorganic acids and organic acids. Exemplary inorganic acids that can be used include mineral acids such as sulfuric acid, nitric acid, hydrochloric acid, hydrofluorosilicic acid and phosphoric acid. Exemplary organic acids that can be used include carboxylic acids including monocarboxylic acids and polycarboxylic acids such as dicarboxcylic acids. Exemplary carboxylic acids include aliphatic and aromatic carboxylic acids. Exemplary aliphatic carboxylic acids include acetic acid, formic acid, halogen-containing carboxylic acids such as chloroacetic carboxylic acid, and modified carboxylic acids containing side groups such —OH, —R, —OR, -(EO)$_x$, —(PO)$_x$, —NH$_2$, and —NO$_2$ wherein R is a $C_1$ to $C_{10}$ alkyl group. Exemplary aromatic carboxylic acids include benzoic carboxylic acid, salicylic carboxylic acid, and aromatic carboxylic acid modified to include as a side group at least one of halogen, —OH, —R, —OR, -(EO)$_x$, —(PO)$_x$, —NH$_2$, and —NO$_2$ wherein R is a $C_1$ to $C_{10}$ alkyl group. Additional exemplary organic acids include oxalic acid, phthlaic acid, sebacic acid, adipic acid, citric acid, maleic acid, and modified forms thereof containing side groups including halogen, —OH, —R, —OR, -(EO)$_x$, —(PO)$_x$, —NH$_2$, and —NO$_2$ wherein R is a C.sub.1 to C.sub.10 alkyl group. It should be understood that the subscript "x" refers to repeating units. Additional exemplary organic acids include fatty acids such as aliphatic fatty acids and aromatic fatty acids. Exemplary aliphatic fatty acids include oleic acid, palmitic acid, stearic acid, C.sub.3-C.sub.26 fatty acids that may be saturated or unsaturated, and sulfonated forms of fatty acids. An exemplary aromatic fatty acid includes phenylstearic acid. Additional acids that can be used include peroxycarboxylic acid such as peroxyacetic acid, and phthalimidopercarboxylic acids. Additional acidic pH adjusting agents include carbon dioxide and ozone.

In alternative embodiments, a pH modification providing an increase in pH may occur through the use of an alkaline agent. Exemplary alkaline agents include alkali metal hydroxides, such as sodium hydroxide, potassium hydroxide, and mixtures thereof, alkali metal silicates such as sodium metal silicate, alkaline metal carbonates, alkaline metal bicarbonates, alkaline metal sesquicarbonates, and alkaline metal borates.

Those skilled in the art will recognize, or be able to ascertain using no more than routine experimentation, numerous equivalents to the specific procedures, embodiments, claims, and examples described herein. Such equivalents are considered to be within the scope of this invention and covered by the claims appended hereto. The contents of all references, patents, and patent applications cited throughout this application are hereby incorporated by reference to the same extent as if each individual publication or patent application was specifically and individually indicated as incorporated by reference. All publications and patent applications in this specification are indicative of the level of ordinary skill in the art to which this invention pertains. The invention is further illustrated by the following examples, which should not be construed as further limiting.

EXAMPLES

Embodiments of the present invention are further defined in the following non-limiting Examples. It should be understood that these Examples, while indicating certain embodiments of the invention, are given by way of illustration only. From the above discussion and these Examples, one skilled in the art can ascertain the essential characteristics of this invention, and without departing from the spirit and scope thereof, can make various changes and modifications of the embodiments of the invention to adapt it to various usages and conditions. Thus, various modifications of the embodiments of the invention, in addition to those shown and described herein, will be apparent to those skilled in the art from the foregoing description. Such modifications are also intended to fall within the scope of the appended claims.

Example 1

The percentage stain removal of various stains was analyzed by comparing the efficacy of stain removal using both a percarboxylic acid composition generated according to the invention compared to a commercial standard. The percarboxylic acid compositions were generated using an adjustable biocide formulator (ABF) apparatus or system for on-site generation of peracid chemistries. Further description of the ABF apparatus and/or system is disclosed in related applications U.S. Patent Application Publication Nos. U.S. 2012/0322872, U.S. 2012/0172437 and U.S. 2012/0171076, which are hereby expressly incorporated herein by reference.

The commercial standard used for comparison was Turbo Oxysan® (Ecolab, Inc.), a commercially available textile bleach/disinfectant was used as the control (indicated for use in Europe at 40° C.). The control bleach/disinfectant was used to demonstrate the benefits afforded by the use of the ABF generated peracids according to the invention which do not have the same limitations as the commercially available textile bleach/disinfectant, including for example requirements for shipment to a point of use, storage of the peracid chemistry, additional agents required for stability and such storage, addition expense of using more reagents (e.g. hydrotropes and other ingredients), potential for malodors upon degradation of peracids, etc.

Stains from coffee, curry and tea were tested on swatches as outlined below. Stain removal was evaluated according to detergency testing methods using a tergotometer. The tergotometer contains six pots filled with 1 L of water sitting in a temperature controlled water bath. A HunterLab Color Quest spectrophotometer was used to determine the lightness or darkness of each swatch, as measured by the L* value, prior to treatment. During each tergotometer run, the swatches and the test chemistry (whether control or alkaline generated peracids) were added to the wash solution and agitated for 10 min. After completion of that time the swatches were removed from pots, rinsed with cold water, and dried at room temperature overnight. After drying, the swatches were again read on the spectrophotometer to determine the post-wash L* value. The % stain removal is calculated from the difference between the initial (before washing) L* value and the final L* value (after washing).

In laundry soil is something that is physical removed from textiles by a combination of chemical detergents, heat, and mechanical action. By contrast, stains are not removed by conventional detergents. Bleaches, typically oxidative, work to destroy the colored chromophore in stains, thus causing the color to lessen. Coffee, curry and tea are examples of stains where the color on a textile will lighten as a result of the oxidative action of bleach. The bleaching activity of two different ABF generated peracid systems was compared to the commercial standard of Turbo Oxysan®. An ABF peroxyoctanoic acid (POOA) alone was tested as well as a mixed peracid system with both peroxyoctanoic acid (POOA) and peroxyacetic acid (POAA). Formulation differences between Turbo Oxysan®, the ingredients used to generate the ABF peroxyoctanoic acid (POOA) composition and the ABF mixed peroxyacid (POOA and POAA) composition are shown in Table 1.

TABLE 1

|  | Turbo Oxysan ® | ABF POOA Amounts (grams) for formulas tested in Ex. 1 | ABF POOA/POAA |
|---|---|---|---|
| Sorbitan octanoate |  | 8.23 | 8.21 |
| Water | 73.17 | 69.75 |  |
| 35% hydrogen peroxide |  | 9.8 | 9.89 |
| 50% sodium hydroxide |  | 8.84 | 8.78 |
| Triacetin |  | 0 | 3.52 |
| Titrated Peracid Levels (%) |  |  |  |
| POAA | 5.4 | — | 3.3 |
| POOA | 1.5 | 2.6 | 2.7 |

The use pH was standardized at 8 between the three systems. The percentage stain removal of the tested systems is shown in Table 2.

TABLE 2

|  | % Removal of Stains from ABF Peracids vs. commercial control | | |
|---|---|---|---|
|  | Turbo Oxysan ® | ABF POOA | ABF POOA/POAA |
| Coffee on Poly/cotton | 40.5 | 40.6 | 43.6 |
| Curry on Cotton | 14.2 | 33.5 | 24.4 |
| Tea on Cotton | 29.5 | 23.7 | 30.4 |
| Tea on Poly/cotton | 42.3 | 40.5 | 45.2 |

As shown in Table 2, the ABF POOA alone gives performance that is clearly superior over the control on the curry stain, but slightly deficient on tea. The mixed peracid ABF system is superior to the control on all stains tested.

Example 2

The antimicrobial efficacy of ABF generated peracid systems according to the invention was tested on textiles. The bactericidal efficacy of the ABF generated single peroxyacid (POAA or POOA) composition shown in Table 3 were generated according to the amount (%) of each raw material used to generate the ABF peracid systems to determine antimicrobial efficacy. The systems were titrated to be 2.03% POAA and 4.09% POOA, respectively.

The chemistries were tested against *Staphylococcus aureus* ATCC 6538, *Enterococcus hirae* ATCC 10541, and *Escherichia coli* ATCC 10536. The analysis was conducted according to European Standard EN1276: *Quantitative Suspension Test for the Evaluation of Bactericidal Activity of Chemical Disinfectants and Antiseptics used in Food, Industrial, Domestic and Institutional Areas*. EN 1276 standard conditions include: 15 ppm POOA, 25 ppm POAA, pH 3.5, 5 min, 20° C. in the presence of soil. Results are shown in Table 4.

TABLE 3

|  | POAA Amt (%) for Formula tested | POOA Amt (%) for Formula tested |
|---|---|---|
| Water | 42.31 | 13.4 |
| 35% Hydrogen Peroxide | 10.58 | 14.3 |
| 10% Sodium Hydroxide | 42.21 | 61.5 |
| Triacetin | 4.90 | — |
| Mono/Diglycerol octanoate | — | 10.8 |

TABLE 4

| Organism | Log Reduction |
|---|---|
| *Staphylococcus aureus* | >5.28 |
| *Enterococcus hirae* | >5.15 |
| *Escherichia coli* | >5.20 |

The ABF generated mixed peroxyacid composition gave a greater than 5 log reduction on all bacteria tested, exceeding the 5 log threshold required to pass EN 1276 standard for antimicrobial efficacy.

Example 3

The sporicidal efficacy of ABF generated peracid and peroxyacid compositions according to the invention was also tested. In addition to bactericidal activity, the ABF systems have efficacy against spores such as *Clostridium difficile*, which are typically more difficult to eradicate than bacteria. The sporicidal efficacy of the ABF generated mixed peroxyacid (POAA/POOA) composition of Example 1 was tested against *Clostridium difficile* ATCC 700792 using the European Standard EN13704: *Quantitative Suspension Test for the Evaluation of Sporicidal Activity of Chemical Disinfectants and Antiseptics used in Food, Industrial, Domestic and Institutional Areas*. EN 13704 defines sporicidal activity as the "capability of the product to produce at least a $10^3$ reduction in the number of bacterial spores under conditions defined by this European Standard."

Further description of the test system are provided: Test System: *Clostridium difficile* ATCC 700792. Interfering Substance: Clean Conditions Bovine Albumin Solution (0.3 g/100 mL). Test Temperature: 40° C.±1° C.; 28 ppm POOA+92 ppm POAA: 30° C.±1° C. Exposure Time: 10 minutes, 20 minute, 30 minutes and 40 minutes. Neutralizer Media: 8 mL 0.5% Sodium Thiosulfate+1 mL MilliQ Water. A neutralizer screen was performed as part of the testing, verified that the neutralizer adequately neutralized the product and was not detrimental to the tested organisms. Plating Medium: Cycloserine-Cefoxitin Fructose Agar w/HS (CCFA-HT)-purchased from Anaerobe Systems. Incubation: 35° C. for 72 hours anaerobically.

The objective of the micro efficacy testing was to observe sporicidal synergy between the individual components of ABF mixtures against the *Clostridium difficile* ATCC 700792 at 10 minute, 20 minute, 30 minute and 40 minute exposure times. The lowest ABF mixture concentration tested was deconstructed to evaluate for synergy between combinations of POOA, POAA and Turbo emulsion surfactant.

In addition, an ABF mixture of 28 ppm POOA+92ppm POAA (equivalent to Turbo Oxysan control concentrations) was tested at a lower temperature of 30° C., as opposed to 40° C. that it was tested earlier in order to observe if sporicidal efficacy can still be achieved at a lower temperature.

TABLE 5

ABF POOA Mixture

| Raw Material | Amount (g) |
|---|---|
| Glycerol Octanoate | 10.10 g |
| H2O2 (35%) | 13.37 g |
| DI H2O | 18.94 g |
| NaOH (10%) | 57.60 g |

Titrated to be 3.66% POOA

TABLE 6

ABF POAA Mixture

| Raw Material | Amount (g) |
|---|---|
| Triacetin | 4.9 g |
| H2O2 (35%) | 10.58 g |
| DI H2O | 42.31 g |
| NaOH (10%) | 42.21 g |

Titrated to be 4.00% POAA

TABLE 7

Test Substance Dilution

| Test Substance | Desired Concentration* | Diluent | Test Solution (Volume of Test Substance/Total Volume) | pH** |
|---|---|---|---|---|
| POOA + POAA | 11 ppm POOA + 38 ppm POAA | Sterile MilliQ Water | 0.0573 g + 0.2054 g/ 200 g Total | 7.59 |
| POOA + Turbo emulsion | 11 ppm POOA + 2625 ppm TE | | 0.0601 g + 0.525 g TE/ 200 g Total | 7.50 |
| POOA | 11 ppm POOA | | 0.0601 g/200 g Total | 7.53 |
| POAA + Turbo emulsion | 38 ppm POAA + 2625 ppm TE | | 0.190 g + 0.525 g TE/ 200 g Total | 7.54 |
| POAA | 38 ppm POAA | | 0.190 g/200 g Total | 7.51 |
| POOA + POAA | 28 ppm POOA + 92 ppm POAA | | 0.153 g + 0.460 g/ 200 g Total | 7.51 |
| POOA + POAA + Turbo emulsion | 11 ppm POOA + 38 ppm POAA + 2625 ppm TE | | 0.0573 g + 0.2054 g + −.525 g TE/200 g Total | 7.57 |

*EN 13704 requires the concentration of the test solution to be 1.25 times the desired test concentration
**pH adjusted to approximately 7.50 by Phosphoric acid

TABLE 8

Test Substance Dilution

| Test Substance | Exposure Time | Average CFU/mL* | Average Log10 Survivors | Log Reduction |
|---|---|---|---|---|
| 11 ppm POOA + 38 ppm POAA pH 7.59 | 10 min | $4.8 \times 10_4$ | 4.68 | 1.71 |
| | 20 min | $2.9 \times 10_4$ | 4.46 | 1.93 |
| | 30 min | $1.6 \times 10_4$ | 4.41 | 1.98 |
| | 40 min | $2.6 \times 10_4$ | 4.20 | 2.19 |
| 11 ppm POOA + Surfactant pH 7.50 | 10 min | $2.6 \times 10_5$ | 5.41 | 1.07 |
| | 20 min | $1.6 \times 10_5$ | 5.20 | 1.28 |
| | 30 min | $1.6 \times 105$ | 5.20 | 1.28 |
| | 40 min | $1.7 \times 10_5$ | 5.23 | 1.25 |
| 11 ppm POOA pH 7.53 | 10 min | $1.49 \times 10_6$ | 6.17 | 0.31 |
| | 20 min | $1.54 \times 10_6$ | 6.19 | 0.29 |
| | 30 min | $1.48 \times 10_6$ | 6.17 | 0.31 |
| | 40 min | $1.44 \times 10_6$ | 6.16 | 0.32 |
| 38 ppm POAA + Surfactant pH 7.54 | 0 min | $1.52 \times 10_6$ | 6.18 | 0.30 |
| | 20 min | $8.1 \times 10_5$ | 5.91 | 0.57 |
| | 30 min | $2.6 \times 10_5$ | 5.41 | 1.07 |
| | 40 min | $1.3 \times 10_5$ | 5.11 | 1.37 |
| 38 ppm POAA pH 7.51 | 10 min | $1.25 \times 10_6$ | 6.10 | 0.38 |
| | 20 min | $1.09 \times 10_6$ | 6.04 | 0.44 |
| | 30 min | $9.7 \times 10_5$ | 5.99 | 0.49 |
| | 40 min | $9.1 \times 10_5$ | 5.96 | 0.52 |
| 28 ppm POOA + 92 ppm POAA pH 7.51 | 10 min | $8.0 \times 104$ | 4.90 | 1.58 |
| | 20 min | $3.1 \times 104$ | 4.49 | 1.99 |
| | 30 min | $1.0 \times 104$ | 4.00 | 2.48 |
| | 40 min | $1.0 \times 104$ | 4.00 | 2.48 |
| 11 ppm POOA + 38 ppm POAA + TE pH 7.57 | 10 min | $4.0 \times 10_3$ | 3.60 | 2.79 |
| | 20 min | $6.2 \times 10_2$ | 2.79 | 3.60 |
| | 30 min | $1.4 \times 10_2$ | 2.15 | 4.24 |
| | 40 min | $8.0 \times 10_1$ | 1.90 | 4.49 |

*Average CFU/mL x 10 (mL neutralizer)

TABLE 9

Post Use-Solution Titration

| Desired Concentration (ppm) | | | Rep | Sample g | EP1 (mL 0.10N Thio) | Measured as ppm POAA | Av. ppm POAA |
|---|---|---|---|---|---|---|---|
| POOA | POAA | TE | | | | | |
| 11 | 38 | 0 | 1 | 87.85 | 0.44 | 19.03 | 18.3 |
| | | | 2 | 112.58 | 0.52 | 17.55 | |
| 11 | 38 | 2625 | 1 | 80.51 | 0.48 | 22.66 | 22.7 |
| | | | 2 | 113.66 | 0.68 | 22.73 | |

EN 13704 defines sporicidal activity as the capability of the product to produce at least a $10^3$ reduction in the number of bacterial spores under conditions defined by this European Standard. FIG. 1 illustrates the log reductions of *C. difficile* spores observed for each test substance at 10, 20, 30 and 40 minute contact times at 40° C., as compared to the complete composition (11 ppm POOA+38 ppm POAA+Surfactant).

All use-solutions were titrated after testing, to ensure an acceptable level of peracid was present in the test solution. None of the individual components achieved a greater than 3 log reduction of *C. difficile* spores and therefore have failed this EN 13704 sporicidal activity screen.

The mixed peracid chemistry system with surfactant (11 ppm POOA+38 ppm POAA+Turbo Emulsion) was the only solution to achieve a greater than 3 log reduction of *C. difficile* spores after 20, 30 and 40 minute exposure times, passing the sporicidal activity screen.

The data shows a significant level of synergy occurring between the (1) POOA and POAA (mixed peracid system) and the (2) peracid and surfactant. Accordingly, there is not only a synergistic relationship resulting from a combination of peracids, but an even greater benefit when the peracid combination is used with surfactants.

As one skilled in the art will ascertain, the amount of time required to for exposure (e.g. 20 minutes) to yield the $10^3$ reduction can be reduced as the peracid concentration is increased. It is expected that the $10^3$ threshold can be passed after 10 min exposure with increased peracid concentration according to the invention. This matches the performance from the commercial disinfectant Turbo Oxysan® disclosed herein.

Example 4

The sporicidal efficacy of ABF generated peracid and peroxyacid compositions according to the invention was compared to a control (commercially-available Turbo Oxysan®) on textiles. The log reduction of *C. difficile* spores was analyzed after treatment with the ABF generated mixed peroxyacid (POAA/POOA) composition of Example 1, compared to the commercial disinfectant Turbo Oxysan®. Both systems used the commercially-available detergent Turbo Emulsion®, dosed at 2625 ppm.

TABLE 10

| Test Substance | Exposure Time | Log Reduction |
|---|---|---|
| Turbo Oxysan ® | 10 minutes | >3.70 |
|  | 20 minutes | >3.70 |
|  | 30 minutes | >3.70 |
|  | 40 minutes | >3.70 |
| 28 ppm POOA + 92 ppm POAA | 10 minutes | >3.70 |
|  | 20 minutes | >3.70 |
|  | 30 minutes | >3.70 |
|  | 40 minutes | >3.70 |

As shown in Table 10, the ABF generated peracid compositions according to the invention perform equivalently to the commercially available equilibrium peracid Turbo Oxysan®, with all other factors held constant.

Example 5

It is well known to those skilled in the art that peroxyacids give optimal bleaching, i.e. stain removal, close to the pKa of the peracid. With a pKa of 8.2, the bleaching from peroxyacetic acid at a low alkaline pH, i.e. 8, is superior to bleaching at a more alkaline pH, e.g. pH 11. Peroxyacid systems (POOA alone or mixed POAA/POOA) were generated according to the method of example 1. Bleaching from those systems was tested in the tergotometer. In one instance the alkaline peracid systems were added to the tergotometer pots without any external pH adjustment. In another instance, sulfuric acid was added to the alkaline peracid solutions to lower the use solution to pH 8. As can be seen in Table 11, when the pH is lowered, there was a significant increase in bleaching for both systems on all swatches tested. This demonstrates that alkaline peracids generated via the method of this invention behave similarly to those generated through a conventional acid equilibrium.

TABLE 11

|  | % Removal of Stains from ABF Peracids at different pH | | | |
|---|---|---|---|---|
|  | POOA alone | | POAA/POOA | |
|  | pH 8 | pH 11 | pH 8 | pH 11 |
| Coffee on Poly/cotton | 40.6 | 21.9 | 43.6 | 23.8 |
| Curry on Cotton | 33.4 | 6.6 | 24.4 | 6.2 |
| Tea on Cotton | 23.6 | 17.8 | 30.4 | 15.7 |
| Tea on Poly/cotton | 40.5 | 21.2 | 45.2 | 23.2 |

The inventions being thus described, it will be obvious that the same may be varied in many ways. Such variations are not to be regarded as a departure from the spirit and scope of the inventions and all such modifications are intended to be included within the scope of the following claims.

What is claimed is:

1. A method for forming a single percarboxylic acid composition for bleaching, antimicrobial, sanitizing and/or disinfecting applications comprising:
   (a) providing a reaction mixture comprising:
      (i) at least one ester of a polyhydric alcohol and a C1 to C18 carboxylic acid;
      (ii) a source of alkalinity; and
      (iii) an oxidizing agent, wherein the reaction mixture has a pH greater than about 12.5, is stable, is not at equilibrium, and is substantially free of a stabilizing agent; and
   (b) allowing the reaction mixture to react for a sufficient amount of time such that at least one C1 to C18 percarboxylic acid is generated to form a peroxycarboxylic acid composition ex situ from said bleaching, antimicrobial, sanitizing and/or disinfecting application.

2. The method of claim 1, further comprising providing said composition with a surfactant source for synergistic antimicrobial, sanitizing and/or disinfectant efficacy at a point of use.

3. The method of claim 1, wherein the pH is greater than about 13.

4. The method of claim 1, wherein the carboxylic acid comprises a C5 to C11 carboxylic acid and wherein the polyhydric alcohol is selected from the group consisting of a sugar, a sugar alcohol, and mixtures and derivatives thereof.

5. The method of claim 1, wherein the sugar alcohol is selected from the group consisting of ethylene glycol, propylene glycol, glycerol, sorbitol, sorbitan, and mixtures and derivatives thereof and wherein the ester is selected from the group consisting of monooctanoic glyceride, dioctanoic glyceride, trioctaonoic glyceride, sorbitan monooctanoate, sorbitan dioctanoate, sorbitan trioctanoate, laurate sucroside and mixtures and derivatives thereof and wherein the oxidizing agent comprises a hydrogen peroxide donor.

6. The method of claim 1, wherein the oxidizing agent comprises a peroxide source selected from the group consisting of a percarbonate, a perborate, hydrogen peroxide, urea hydrogen peroxide, PVT-peroxides and mixtures thereof.

7. The method of claim 1, wherein the source of alkalinity is selected from the group consisting of an alkaline metal hydroxide, an alkaline earth metal hydroxide, an alkali metal silicate, an alkali metal carbonate, borates and mixtures thereof.

8. The method of claim 1, wherein the reaction mixture is comprised of (i) a first reagent premix comprising said ester of a polyhydric alcohol and a C1 to C18 carboxylic acid and said oxidizing agent, and (ii) a second reagent source comprising said source of alkalinity, wherein said reagent premix further comprises at least one reagent selected from the group consisting of a dispersing agent, a solvent, water and mixtures thereof.

9. The method of claim 8, wherein said solvent is an organic solvent to solubilize the ester.

10. The method of claim 8, wherein said dispersing agent is sufficient to create a physically meta-stable solution upon reaction with a source of alkalinity.

11. The method of claim 1, wherein said point of use is a washing machine.

12. The method of claim 11, wherein said point of use is a drum interior, tunnel washer, vertical washer wheel or commercial washing machine.

13. The method of claim 11, wherein said point of use is a textile surface.

14. The method of claim 1, further comprising acidifying said composition to a pH of about 1.0 to about 8.0 ex situ from said point of use or at a point of use.

15. A method for forming a mixed percarboxylic acid composition comprising
  (a) providing a reaction mixture comprising:
    (i) a first ester of a polyhydric alcohol and a C1 to C18 carboxylic acid;
    (ii) a source of alkalinity; and
    (iii) an oxidizing agent;
  (b) allowing the reaction mixture to react for a sufficient amount of time, and then adding a second ester of a polyhydric alcohol and a C1 to C18; and
  (c) after addition of the second ester allowing the mixture to react for a sufficient amount of time such that a mixed peroxycarboxylic acid composition forms ex situ from a bleaching, antimicrobial, sanitizing and/or and disinfecting application; wherein the reaction mixture has a pH greater than about 12.5, is stable, is not at equilibrium, and is substantially free of a stabilizing agent.

16. The method of claim 15, further comprising providing said composition with a surfactant source for synergistic antimicrobial, sanitizing and/or disinfectant efficacy at a point of use.

17. The method of claim 15, wherein the pH is greater than about 13 and wherein said two esters include a C1 to C4 carboxylic acid ester and a C5 to C11 carboxylic acid ester, wherein said esters are selected from the group consisting of triacetin, sorbitan octanoate, glycerol octanoate and mixtures thereof, and wherein said polyhydric alcohol is selected from the group consisting of a sugar, a sugar alcohol, and mixtures and derivatives thereof.

18. The method of claim 15, wherein the sugar alcohol is selected from the group consisting of ethylene glycol, propylene glycol, glycerol, sorbitol, sorbitan, and mixtures and derivatives thereof and wherein the ester is selected from the group consisting of monooctanoic glyceride, dioctanoic glyceride, trioctaonoic glyceride, sorbitan rnonooctanoate, sorbitan dioctanoate, sorbitan trioctanoate, laurate sucroside and mixtures and derivatives thereof and wherein the oxidizing agent comprises a hydrogen peroxide donor.

19. The method of claim 15, wherein the oxidizing agent comprises a peroxide source selected from the group consisting of a percarbonate, a perborate, hydrogen peroxide, urea hydrogen peroxide, PVP-peroxides and mixtures thereof, and wherein the source of alkalinity is selected from the group consisting of an alkaline metal hydroxide, an alkaline earth metal hydroxide, an alkali metal silicate, an alkali metal carbonate, borates and mixtures thereof.

20. The method of claim 15, wherein the reaction mixture is comprised of (i) a first reagent premix comprising said ester of a polyhydric alcohol and a C1 to C18 carboxylic acid and said oxidizing agent, and (ii) a second reagent source comprising said source of alkalinity, wherein said reagent premix further comprises at least one reagent selected from the group consisting of a dispersing agent, a solvent, water and mixtures thereof.

21. The method of claim 20, Wherein said solvent is an organic solvent to solubi lize the ester and wherein said dispersing agent is sufficient to create a physically meta-stable solution upon reaction with a source of alkalinity.

22. The method of claim 15, wherein said point of use is selected from the group consisting of a textile surface, a drum interior and a washer wheel of a commercial or tunnel washing machine.

23. The method of claim 15, further comprising acidifying said composition to a pH of about 1.0 to about 8.0 ex situ from said point of use or at a point of use.

24. A method for bleaching, antimicrobial activity, sanitizing and/or disinfecting a surface comprising:
  (a) forming a single or mixed peroxycarboxy lie acid bleaching and disinfecting composition having an active peroxycarboxylic acid content from about 0.25% to about 20% ex situ from a point of use by reacting a composition comprising at least one ester of a polyhydric alcohol and a C1 to C18 carboxylic acid, a source of alkalinity, and an oxidizing agent, wherein said peroxycarboxylic acid composition is stable and has a pH greater than 12.5; and
  (b) contacting said surface at a point of use with said peroxycarboxylic acid composition and optionally a surfactant source for synergistic efficacy.

25. The method of claim 24, wherein said ex situ generated peroxycarboxylic acid composition is further diluted and/or acidified prior to contacting said surface.

26. The method of claim 24, wherein said point of use is selected from the group consisting of a textile surface, a drum interior and a washer wheel of a commercial or tunnel washing machine.

* * * * *

UNITED STATES PATENT AND TRADEMARK OFFICE
CERTIFICATE OF CORRECTION

| | |
|---|---|
| PATENT NO. | : 8,729,296 B2 |
| APPLICATION NO. | : 13/331104 |
| DATED | : May 20, 2014 |
| INVENTOR(S) | : Jonathan P. Fast et al. |

Page 1 of 1

It is certified that error appears in the above-identified patent and that said Letters Patent is hereby corrected as shown below:

In the Claims:

Col. 33, Claim 6, Line 2:
DELETE after hydrogen peroxide, "PVT-peroxides"
ADD after hydrogen peroxide, --PVP-peroxides--

Col. 34, Claim 21, Line 25:
DELETE after to "solubi lize the"
ADD after to --solubilize the--

Col. 34, Claim 24, Line 37:
DELETE after mixed "peroxycaboxy lie"
ADD after mixed --peroxycarboxylic--

Signed and Sealed this
Fifth Day of August, 2014

Michelle K. Lee
*Deputy Director of the United States Patent and Trademark Office*